(12) United States Patent
Scharschmidt et al.

(10) Patent No.: US 9,289,406 B2
(45) Date of Patent: Mar. 22, 2016

(54) METHODS OF ADMINISTERING AND EVALUATING NITROGEN SCAVENGING DRUGS FOR THE TREATMENT OF HEPATIC ENCEPHALOPATHY

(71) Applicant: HYPERION THERAPEUTICS, INC., Brisbane, CA (US)

(72) Inventors: Bruce Scharschmidt, San Francisco, CA (US); Masoud Mokhtarani, Walnut Creek, CA (US)

(73) Assignee: Horizon Therapeutics, Inc., Lake Forest, IL (US)

(*) Notice: Subject to any disclaimer, the term of this patent is extended or adjusted under 35 U.S.C. 154(b) by 0 days.

(21) Appl. No.: 14/086,870

(22) Filed: Nov. 21, 2013

(65) Prior Publication Data

US 2014/0142186 A1    May 22, 2014

Related U.S. Application Data

(60) Provisional application No. 61/728,967, filed on Nov. 21, 2012, provisional application No. 61/759,292, filed on Jan. 31, 2013.

(51) Int. Cl.
*A61K 31/235*    (2006.01)
*A61K 31/192*    (2006.01)

(52) U.S. Cl.
CPC .................................. *A61K 31/192* (2013.01)

(58) Field of Classification Search
CPC ............... A61K 31/192; A61K 31/194; Y10T 436/175383
USPC .................................. 514/532, 533, 568, 570
See application file for complete search history.

(56) References Cited

U.S. PATENT DOCUMENTS

| | | | |
|---|---|---|---|
| 4,284,647 A | 8/1981 | Brusilow | |
| 4,457,942 A | 7/1984 | Brusilow | |
| 5,654,333 A | 8/1997 | Samid | |
| 5,968,979 A * | 10/1999 | Brusilow | 514/533 |
| 6,060,510 A | 5/2000 | Brusilow | |
| 6,083,984 A | 7/2000 | Brusilow | |
| 6,219,567 B1 | 4/2001 | Eggers | |
| 8,094,521 B2 | 1/2012 | Levy | |
| 8,404,215 B1 * | 3/2013 | Scharschmidt et al. | 424/9.2 |
| 8,642,012 B2 * | 2/2014 | Scharschmidt | 424/9.2 |
| 9,078,865 B2 | 7/2015 | Lee | |
| 2003/0195255 A1 | 10/2003 | Summar | |
| 2004/0229948 A1 * | 11/2004 | Summar et al. | 514/547 |
| 2005/0273359 A1 | 12/2005 | Young | |
| 2006/0135612 A1 | 6/2006 | Ferrante | |
| 2008/0119554 A1 | 5/2008 | Jalan | |
| 2010/0008859 A1 | 1/2010 | Scharschmidt | |
| 2010/0016207 A1 | 1/2010 | Wurtman | |
| 2012/0022157 A1 | 1/2012 | Scharschmidt | |
| 2012/0220661 A1 | 8/2012 | Lee | |
| 2013/0210914 A1 | 8/2013 | Scharschmidt et al. | |
| 2013/0281530 A1 * | 10/2013 | Scharschmidt et al. | 514/533 |
| 2015/0094278 A1 | 4/2015 | Scharschmidt | |
| 2015/0105469 A1 | 4/2015 | Scharschmidt | |

FOREIGN PATENT DOCUMENTS

| | | |
|---|---|---|
| WO | WO94/22494 | 10/1994 |
| WO | WO 2005/053607 | 6/2005 |
| WO | WO 2006/056794 | 6/2006 |
| WO | WO 2007/005633 | 1/2007 |
| WO | WO 2009/087474 | 7/2009 |
| WO | 2009/134460 | 11/2009 |
| WO | 2010/025303 | 3/2010 |
| WO | WO 2012/028620 | 3/2012 |
| WO | WO2013/048558 | 4/2013 |
| WO | WO2013/158145 | 10/2013 |

OTHER PUBLICATIONS

Brusilow, S. W., et al., "Amino Acid Acylation: A Mechanism of Nitrogen Excretion in Inborn Errors of Urea Synthesis," Science 207:659-661 (1980).

Brusilow, S. W., "Phenylacetylglutamine May Replace Urea as a Vehicle for Waste Nitrogen Excretion," Pediatr. Res. 29(2):147-150 (1991).

Diaz, G.A., et al., "Phase 3 Blinded, Randomized, Crossover Comparison of Sodium Phenylbutyrate (NaPBA) and Glycerol Phenylbutyrate (GPB): Ammonia (NH3) Control in Adults with Urea Cycle Disorders (UCDS)," Mol. Genet. Metab. 102:276 (2011).

Enns, G. M., et al., "Survival After Treatment with Phenylacetate and Benzoate for Urea-Cycle Disorders," New Engl. J. Med. 356:2282-2292 (2007).

Lee, B., et al., "Phase 2 Comparison of a Novel Ammonia Scavenging Agent with Sodium Phenylbutyrate in Patients with Urea Cycle Disorders: Safety, Pharmacokinetics and Ammonia Control," Mol. Genet. Metab. 100(3):221-228 (2010).

Lichter-Konecki, U., et al., "Ammonia Control in Children with Urea Cycle Disorders (UCDs): Phase 2 Comparison of Sodium Phenylbutyrate and Glycerol Phenylbutyrate," Mol. Genet. Metab. 103:323-329 (2011).

McGuire, B. M., et al., "Pharmacology and Safety of Glycerol Phenylbutyrate in Healthy Adults and Adults with Cirrhosis," Hepatolog Stauch, S., et al., "Oral L-Ornithine-L-Aspartate Therapy of Chronic Hepatic Encephalopathy: Results of a Placebo-Controlled Double-Blind Study," J. Hepatol. 28:856-864 (1998).

United States Patent and Trademark Office, International Search Report and Written Opinion dated Mar. 28, 2014 for PCT/US13/71333.

Ambrose, A.M., (1933) "Further Studies on the Detoxification of Phyenylacetic Acid." *J Biol Chem* 101:669-675. y 51:2077-2085 (2010).

(Continued)

*Primary Examiner* — My-Chau T Tran

(57) ABSTRACT

The present disclosure provides methods for treating hepatic encephalopathy (HE) and for optimizing and adjusting nitrogen scavenging drug dosage for subjects with HE.

6 Claims, 10 Drawing Sheets

(56) References Cited

OTHER PUBLICATIONS

Batshaw M.L. et al. (Dec. 1980) "Treatment of Hyperammonemic Coma Caused by Inborn Errors of Urea Synthesis," *J Pediatr* 97(6):893-900.

Batshaw M.L. et al. (Jun. 10, 1982) "Treatment of Inborn Errors of Urea Synthesis: Activation of Alternative Pathways of Waste Nitrogen Synthesis and Excretion," *N Engl J Med* 306(23):1387-1392.

Batshaw, M.L. (1984) "Hyperammonemia," in Current Problems in Pediatrics, Lockhart, J.D. ed.: Year Book Medical Publishers, pp. 2-69.

Batshaw, M.L. et al. (Aug. 1981) "New Approaches to the Diagnosis and Treatment of Inborn Errors of Urea Synthesis," *Pediatrics* 68(2):290-297.

Berry, G.T. et al., (2001) "Long-term Management of Patients with Urea Cycle Disorders." *J Pediatrics* 138:S56-S61.

Brahe, C., et al., (2005) "Phenylbutyrate Increases SMN Gene Expression in Spinal Muscular Atrophy Patients," *Eur J Hum Genet* 13:256-259.

Brunetti-Pierri, N., et al., (2011) "Phenylbutyrate Therapy for Maple Syrup Urine Disease," *Hum Mol Genet* 20(4):631-640.

Brusilow, S.W., et al. (Sep. 1, 1979) "New Pathways of Nitrogen Excretion in Inborn Errors of Urea Synthesis," *Lancet* 2(8140):452-454.

Brusilow, S.W., et al. (Jun. 21, 1984) "Treatment of Episodic Hyperammonemia in Children With Inborn Errors of Urea Synthesis," *N Engl J Med* 310(25):1630-1634.

Brusilow, S.W., et al. (1991) "Treatment of Urea Cycle Disorders," Chapter 5 in Treatment of Genetic Diseases, Desnik, R.J. et al. eds, Churchill Livingstone, New York, New York, pp. 79-94.

Brusilow, S.W., et al. (1993) "Restoration of Nitrogen Homeostasis in a Man with Ornithine Transcarbamylase Deficiency." *J Metabolism* 42:1336-1339.

Brusilow, S.W., et al. (Jul. 25, 1994—Amendment Dated) "Protocols for Management of Intercurrent Hyperammonemia in Patients with Urea Cycle Disorders," FDA Application to Market a New Drug for Human Use or an Antibiotic Drug for Human Use, 14 pages.

Brusilow, S.W., et al. (1995) "Urea Cycle Disorders: Clinical Paradigm of Hyperammonemic Encephalopathy." *Prog Liver Diseases* 12:293-309.

Brusilow, S.W., et al. (1995) "Urea Cycle Enzymes," Chapter 32 in the Metabolic and Molecular bases of Inherited Diseases, Scriver, C.R. et al. eds., McGraw-Hill, Inc. New York, New York, pp. 1187-1232.

Brusilow, S.W., et al. (1996) "Urea Cycle Disorders: Diagnosis, Pathophysiology, and Therapy," *Adv Pediatr* 43:127-170.

Calloway, D.H. et al. (1971) "Sweat and Miscellaneous Nitrogen Losses in Human Balance Studies," *J Nutrition* 101:775-786.

Calloway, D.H. et al. (1971) "Variation in Endogenous Nitrogen Excretion and Dietary Nitrogen Utilization as Determinants of Human Protein Requirements," *J Nutrition* 101:205-216.

Camacho, L.H. et al. "Phase I Dose Escalation Clinical Trial of Phenyl butyrate Sodium Administered Twice Daily to Patients With Advanced Solid Tumors," *Invest. New Drugs* 25:131-138 (2007, e-pub. Oct. 20, 2006).

Chang, J. et al., (2001) "Treatment of Spinal Muscular Atrophy by Sodium Butyrate," *PNAS* 98(17):9808-9813.

Chung, Y.L., et al., (2000) "A Novel Approach for Nasopharyngeal Carcinoma Treatment Uese Phenylbutyrate as a Protein Kinase C Modulator: Implications for Radiosensitization and EBV-Targeted Therapy," *Clin Cancer Res* 6:1452-1458.

ClinicalTrials.Gov/Archive View of NCT00551200 on Dec. 11, 2007 "Dose-Escalation Safety Study of Glyceryl Tri (4-Phenylbutyrate)(GT4P) to Treat Urea Cycle Disorders" [accessed Oct. 5, 2009], 4 pages.

Comte, B. et al., (2002) "Identification of Phenylbutyrylglutamine, A new Metabolite of Phenylbutyrate Metabolism in Humans," *J Mass Spectrometry*, 37(6):581-590.

Cudkowicz, ALS (2009) "Phase 2 Study of Sodium Phenylbutyrate in ALS," *Amyotrophic Lateral Sclerosis* 10:99-106.

Deferrari, G. et al. (1981) "Brain Metabolism of Amino Acids and Ammonia in Patients with Chronic Renal Insufficiency," *Kidney International* 20:505-510.

FDA Label for Buphenyl, 6 pages.

FDA. "Buphenyl® (Sodium Phenylbutyrate) Label" nine pages. (Aug. 2003).

Gargosky, S. (Aug. 2, 2005) "Improved Survival of Neonates Following Administration of Ammonul® (Sodium Phenyl acetate & Sodium Benzoate) 10% I 10% Injection," SSIEM Poster, six pages.

Gargosky, S. et al. (Oct. 14, 2005) "Results of a Twenty-two Year Clinical Trial: Actue, Adjunctive Pharmacological Treatment of Hyperammonemic Episodes in Patients with Deficiencies in Enzymes of the Urea Cycle," poster, Ucyclyd Pharma, Inc., one page.

Gargosky, S. (2006) "High Ammonia Levels Are Associated With Increased Mortality and Coma," Ucyclyd Pharma, Inc., one page.

Ghabril, M., et al., (2012) "Glycerol Phenylbutyrate (GPB) Administration in Patients with Cirrhosis and Episodic Hepatic Encephalopathy (HE)," accepted for presentation at Digestive Disease Week.

Gropman, A. L., et al., (2008) "1H MRS Allows Brain Phenotype Differentiation in Sisters with Late Onset Ornithine Transcarbamylase Deficiency (OTCD) and Discordant Clinical Presentations," *Mol Genet Metab* 94(1):52-60.

Gropman, A.L. et al. (2008) "1H MRS Identifies Symptomatic and Asymptomatic Subjects With Partial Ornithine Transcarbamylase Deficiency," Mol. Genet. Metab. 95(1-2):21-30 (Sep.-Oct. 2008, e-pub. Jul. 26, 2008).

Gropman, A. (2010) "Brain Imaging in Urea Cycle Disorders," *Mol Genet Metab* 100:S20-S30.

Hines, P., et al., (2008) "Pulsed-Dosing with Oral Sodium Phenylbutyrate Increases Hemoglobin F in a Patient with Sickle Cell Anemia," *Pediatr Blood Cancer* 50:357-359.

Hogarth, P., et al., (2007) "Sodium Phenylbutyrate in Huntington's Disease: A Dose-Finding Study," *Mov Disord* 22(13):1962-1964.

Huang, H.H., et al., (2012) "Cannabinoid Receptor 2 Agonist Ameliorates Mesenteric Angiogenesis and Portosystemic Collaterals in Cirrhotic Rats," *Hepatology* 56:248-258.

Hyperion Therapeutics (Oct. 23, 2007) "Hyperion Therapeutics Announces Enrollment of First Patient in Phase 1/2 Clinical Trial of GT4P in Patients with Urea Cycle Disorders" Announcement, 1 page.

Hyperion Therapeutics. "Hyperion Therapeutics Announces Results for Phase II Study in Urea Cycle Disorders," located at <http://www.hyperiontx.com/press/release/pr1238518388,> last visited on Apr. 27, 2011, three pages. (Mar. 30, 2009).

Hyperion Therapeutics. "Hyperion Therapeutics Announces Results of Phase I Study in Patients with Liver Cirrhosis" located at <http://www.hyperiontx.com/press/release/pr 1243891161>, last visited on Apr. 27, 2011, three pages. (Jun. 2, 2009).

James, M.O. et al. (1972) "The Conjugation of Phenylacetic Acid in Man, Sub-Human Primates and Some Other Non-Primates Species," *Proc R Soc London* 182:25-35.

John, B.A. et al. (Mar. 2009) "The Disposition of HPN-100, A Novel Pharmaceutical Under Development for Potential Treatment of Hyperammonemia, in Cynomolgus Monkeys," ACMG 2009 ADME, poster, two page.

John, B.A. et al. (Mar. 2009) "The Disposition of HPN-100, A Novel Pharmaceutical Under Development for Potential Treatment of Hyperammonemia, in Cynomologus Monkeys," abstract presented at ACMG 2009, one page.

Kasumov, T. et al., (2004) "New Secondary Metabolites of Phenylbutyrate in Humans and Rats," *Drug Metabolism and Disposition* 32(1):10-19.

Lee et al., (2008) "Preliminary data on adult patients with urea cycle disorders (UCD) in an open-label, switch-over dose-escalation study comparing a new ammonia scavenger, glyceryl tri(4-phenylbutyrate) (HPN-100), to buphenyl (sodium phenylbutyrate (PBA))." *J Inherited Metabolic Disease* 31(1):91.

Lee, B. et al. (Aug. 2009) "Dosing and Therapeutic Monitoring of Ammona Scavenging Drugs and Urinary Phenylacetylglutamine (PAGN) as a Biomarker: Lessons From a Phase 2 Comparison of a Novel Ammonia Scavenging Agent with Sodium Phenylbutyrate (NAPBA)," presented at ICIEM 2009, San Diego, CA, poster, one page.

(56) References Cited

OTHER PUBLICATIONS

Lee, B. et al. (Aug. 2009) "Dosing and Therapeutic Monitoring of Ammonia Scavenging Drugs and Urinary Phenylacetylglutamine (PAGN) as a Biomarker; Lessons From a Phase 2 Comparison of a Novel Ammonia Scavenging Agent With Sodium Phenylbutyrate (NaPBA)," abstract presented at ICIEM 2009, San Diego, CA, one page.

Lee, B. et al. (Mar. 2009) "Phase 2 Study of a Novel Ammonia Scavenging Agent in Adults With Urea Cycle Disorders (UCDs)," abstract presented at ACMG 2009, one page.

Lee, B. et al. (Mar. 2009) "Phase 2 Study of a Novel Ammonia Scavenging Agent in Adults with Urea Cycle Disorders (UCDs)," presented at ACMG 2009, seventeen pages.

Lewis, H.B. (1914) "Studies in the Synthesis of Hippuric Acid in the Animal Organism. II. The Synthesis and Rate of Elimination of Hippuric Acid After Benzoate Ingestion in Man," *J Biol Chem* 18:225-231.

Liang, K.Y., et al., (1986) "Longitudinal Data Analysis Using Generalized Linear Models," *Biometrika* 73(1):13-22.

MacArthur, R. B., et al., "Pharmacokinetics of sodium phenylacetate and soium benzoate following intravenous administrtion as both a bolus and continuous infusion to healthy adult volunteers." *Mol Genet Metab* 81:(1):567-573 (2004).

Mansour, A. et al. "Abdominal Operations in Patients with Cirrhosis: Still a Major Surgical Challenge," *Surgery* 122(4):730-735. (Abstract Only.) (Oct. 1997).

Maestri, N. E. et al. "Plasma Glutamine Concentration: A Guide in the Management of Urea Cycle Disorders," *J Pediatr* 121(2):259-261(Aug. 1992).

McGuire, B. et al. (2008) "Pharmacokinetic (PK) Safety Study of Sodium Phenylacetate and Sodium Benzoate Administered to Subjects with Hepatic Impairment," abstract of the 13th International Symposium, Abano (Padova), Italy, Apr. 28-May 1, 2008, two pages.

McGuire, B. et al. (2008) Pharmacokinetic Safety Study of Sodium Phenylacetate and Sodium Benzoate Administered to Subjects With Hepatic Impairments, *Liver International* 28:743. (Abstract Only).

McGuire, B.M. et al. (2009) "Pharmacokinetic (PK) and Safety Analyses of a Novel Ammonia-Reducing Agent in Healthy Adults and Patients with Cirrhosis," Hyperion Therapeutics, poster, one page.

McGuire, B.M. et al. (May 2009) "Pharmacokinetic (PK) and Safety Analyses of a Novel Ammonia-Reducing Agent in Healthy Adults and Patients with Cirrhosis," abstract presented at DDW, two pages.

McQuade P.S. (1984) "Analysis and the Effects of Some Drugs on the Metabolism of Phenylethylamine and Phenylacetic Acid," *Neuropsychopharmaco Biol Psychiat* 8:607-614.

Mercuri, E., et al., (2004) "Pilot Trial of Phenylbutyrate in Spinal Muscular Atrophy," *Neuromuscul Disord* 14:130-135.

Mokhtarani, M., et al., (2012) "Elevated Phenylacetic Acid (PAA) Levels Appear Linked to Neurological Adverse Events in Healthy Adults But Not in Urea Cycle Disorder (UCD) Patients," *Mol Genet Metab* 105:342.

Moldave, K., et al., (1957) "Synthesis of Phenylacetylglutamine by Human Tissue," *J Biol Chem* 229:463-476.

Monteleone, JPR, et al., (2012) "Population pk Analysis of Glycerol Phenylbutyrate (GPB) and Sodium Phenylbutyrate(NAPBA) in Adult and Pediatric Patients with Urea Cycle Discorders," *Mol Genet Metab* 105:343.

Ong, J. P., et al., (2003) "Correlation Between Ammonia Levels and the Severity of Hepatic Encephalopathy," *Am J Med* 114:188-193.

Perrine, S. P., (2008) "Fetal Globin Stimulant Therapies in the Beta-Hemoglobinopathies: Principles and Current Potential," *Pediatr Ann* 37(5):339-346.

Piscitelli, S.C. et al. (1995) "Disposition of Phenylbutyrate and its Metabolites, Phenylacetete and Phenylacetylglutamine," *J Clin Pharmacal* 35:368-373.

Propst, A. et al. (1995) "Prognosis and Life Expectancy in Chronic Liver Disease," *Dig Dis Sci* 40(8):1805-1815. (Abstract Only).

Riley, T.R. et al. (2001) "Preventive Strategies in Chronic Liver Disease: Part II. Cirrhoses," *Am Fam Physician* 64(10):1735-1740. (Abstract Only).

Rudman, D., et al., (1973) "Maximal Rates of Excretion and Synthesis of Urea in Normal and Cirrhotic Subjects," *J Clin Invest* 52:2241-2249.

Ryu, H., et al., (2005) "Sodium Phenylbutyrate Prolongs Survival and Regulates Expression of Anti-Apoptotic Genes in Transgenic Amyotrophic Lateral Sclerosis Mice," *J Neurochem* 93:1087-1098.

Shiple, G.J. et al. (1922) "Synthesis of Amino Acids in Animal Organisms. I. Synthesis of Glycocoll and Glutamine in the Human Organism," *J Am Chem Soc* 44:618-624.

Simell, O., et al. (1986) "Waste nitrogen excretion via amino acid acylation: Benzoate and phyylacetate in lysinuric protein intolerance." *Ped Res* 20(11):1117-1121.

Singh, (2001) "Consensus Statement from a Conference for the Management of Patients with Urea Cycle Disorders," *Suppl to J Pediatrics* 138(1):S1-S5.

Summar, M. et al. (2007) "Description and Outcomes of 316 Urea Cycle Patients From a 21-Year, Multicenter Study of Acute Hyperammonemic Episodes," Abstract, presented at Annual Symposium CCH—Congress Centre Hamburg, Sep. 4-7, 2007, GSSIEM 2007, two pages.

Summar, M.L. et al. "Diagnosis, Symptoms, Frequency and Mortality of 260 Patients with Urea Cycle Disorders From a 21-Year, Multicentre Study of Acute Hyperammonaemic Episodes," *Acta Paediatr* 97:1420-1425 (Oct. 2008, e-pub. Jul. 17, 2008).

Swedish Orphan International, "Urea Cycle Disorders an International Perspective," Poster, Symposium Swedish Orphan International, Barcelona, Spain, Jan. 12, 2007, one pages.

Tanner, L. M., et al., (2007) "Nutrient intake in lysinuric protein intolerance." *J Inherited Metabolic Disease* 30(5):716-721.

Thibault, A. et al., (1994) "A Phase I and Pharmacokinetic Study of Intravenous Phenylacetate in Patients with Cancer," *Cancer Res* 54(7):1690-1694.

Thibault, A., et al., (1995) "Phase I Study of Phenylacetate Administered Twice Daily to Patients with Cancer," *Cancer* 75(12):2932-2938.

Tuchman, M. et al. (2008) "Cross-Sectional Multicenter Study of Patients With Urea Cycle Disorders in the United States," *Malec Genetics Metab* 94:397-402 (e-pub. Jun. 17, 2008).

Waterlow, J.C. (1963) "The Partition of Nitrogen in the Urine of Malnourished Jamaican Infants," *Am J Clin Nutrition* 12:235-240.

Xie, G., et al., (2012) "Role of Differentiation of Liver Sinusoidal Endothelial Cells in Progression and Regression of Hepatic Fibrosis in Rats," *Gastroenterology* 142:S918.

Zeitlin, P.L. et al. (2002) "Evidence of CFTR Function in Cystic Fibrosis After System Administration of 4-Phenylbutyrate," *Mol Therapy* 6(1):119-126.

Combined Search and Examination Report for British Patent Application No. GB0915545.8, search completed Oct. 8, 2009, report dated Oct. 9, 2009.

Combined Search and Examination Report for British Patent Application No. GB1013468.2, search completed Sep. 8, 2010, report dated Sep. 9, 2010.

European Patent Office, Extended European Search Report for EP09739263 completed Nov. 2, 2011.

European Patent Office, International Search Report and Written Opinion for PCT/US2009/055256 completed Dec. 18, 2009 and mailed Dec. 30, 2009.

Examination Report for British Patent Application No. GB0915545.8 dated Feb. 5, 2010.

Examination Report for British Patent Application No. GB0915545.8 dated May 11, 2010.

Examination Report for British Patent Application No. GB0915545.8 dated Oct. 27, 2010.

Examination Report for British Patent Application No. GB1013468.2 dated Oct. 28, 2011.

International Preliminary Report on Patentability (Ch I) for PCT/US2012/028620, completed Jun. 4, 2012 and mailed on Apr. 10, 2014.

International Preliminary Report on Patentability (Ch II) for PCT/US2012/028620, completed Aug. 22, 2013 and mailed Sep. 4, 2013.

(56) References Cited

OTHER PUBLICATIONS

International Preliminary Report on Patentability for PCT/US2009/030362, completed Feb. 24, 2009 and mailed on Mar. 10, 2011.
International Preliminary Report on Patentability for PCT/US2009/055256, completed on Aug. 27, 2009, mailed on Mar. 10, 2011.
United States Patent and Trademark Office, International Search Report and Written Opinion for PCT/US2009/030362 mailed Mar. 2, 2009.
United States Patent and Trademark Office, International Search Report and Written Opinion for PCT/US2012/028620 mailed Jun. 20, 2012.
United States Patent and Trademark Office, International Search Report and Written Opinion for PCT/US2012/54673 mailed Nov. 20, 2012.
Ahrens, M. et al. (Jan. 2001). "Consensus Statement From a Conference for the Management of Patients With Urea Cycle Disorders." Supp. Journal of Pediatrics 138(1):S1-55.
Amodio, P., et al., "Detection of Minimal Hepatic Encephalopathy: Normalization and Optimization of the Psychometric Hepatic Encephalopathy Score. A Neuropsychological and Quantified EEG Study," J. Hepatol. 49:346-353 (2008).
Bajaj, J. S., et al., "Review Article: The Design of Clinical Trials in Hepatic Encephalopathy—An International Society for Hepatic Encephalopathy and Nitrogen Metabolism (ISHEN) Consensus Statement," Aliment Pharmacol Ther. 33 (7):739-747 (2011).
Barsotti, Measurement of Ammonia in Blood, 138 J. Pediatrics, S11-S20 (2001).
Batshaw, et al., Treatment of Carbamyl Phosphate Synthetase Deficiency with Keto Analogues of Essential Amino Acids, The New England J. Medicine, 292, 1085-1090 (1975).
Batshaw, M. L. et. al., Alternative Pathway Therapy for Urea Cycle Disorder: Twenty Years Later, 138 J. Pediatrics S46 (2001).
Blau, Duran, Blaskovics, Gibson (editors), Physician's Guide to the Laboratory Diagnosis of Metabolic Diseases, 261-276 (2d ed. 1996).
Blei A. T., et al., "Hepatic Encephalopathy," Am. J. Gastroenterol. 96(7):1968-1976 (2001).
Burlina, A.B. et al., Long-Term Treatment with Sodium Phenylbutyrate in Ornithine Transcarbamylase-Deficient Patients, 72 Molecular Genetics and Metabolism 351-355 (2001).
Carducci, M., Phenylbutyrate Induces Apoptosis in Human Prostate Cancer and Is More Potent Than Phenylacetate, 2 Clinical Cancer Research 379 (1996).
Carducci, M.A. et al., A Phase I Clinical and Pharmacological Evaluation of Sodium Phenylbutyrate on an 120-h Infusion Schedule, 7 Clin. Cancer Res. 3047 (2001).
Center tor Drug Evaluation and Research, Clinical Pharmacology and Biopharmaceutics Review for New Drug Application No. 20-645 (Ammonul®) (2005).
Center for Drug Evaluation and Research, Labeling for New Drug Application No. 20-645 (Ammonul®) (2005).
Center for Drug Evaluation and Research, Medical Review for New Drug Application No. 20-645 (Ammonul®) (2005).
Chen, Z. et al., Tributyrin: A Prodrug of Butyric Acid for Potential Clinical Application in Differentiation Therapy, 54 Cancer Research 3494 (1994).
Clay, A. et. al, Hyperammonemia in the ICU, 132 Chest 1368 (2007).
Collins, A.F. et al., Oral Sodium Phenylbutyrate Therapy in Homozygous Beta Thalassemia: A Clinical Trial, 85 Blood 43 (1995).
'Complaint for Patent Infringement', *Hyperion Therapeutics, Inc.* v. *Par Pharmaceuticals, Inc.* Filed in U.S. District Court for the Eastern District of Texas, Apr. 23, 2014.
Conn, H. O., et al., "Liver Physiology and Disease: Comparison of Lactulose and Neomycin in the Treatment of Chronic Portal-Systemic Encephalopathy. A Double Blind Controlled Trial," Gastroenterology 72(4):573-583 (1977).
Cordoba, J., "New Assessment of Hepatic Encephalopathy," Journal of Hepatology 54: 1030-1040 (2011).
Darmaun, D. et al., Phenylbutyrate-Induced Glutamine Depletion in Humans: Effect on Leucine Metabolism, 5 Am. J. of Physiology: Endocrinology and Metabolism E801 (1998).
Darzens, G. et al.: "Preparation de quelques glycerides phenylaliphatiques et leur reduction en alcools . . . ", Comptes Rendus Hebdomadaires Des Seances De L'Academie Des Sciences., vol. 205, Oct. 18, 1937, pp. 682-684.
Diaz, G. A., et al., "Ammonia Control and Neurocognitive Outcome Among Urea Cycle Disorder Patients Treated with Glycerol Phenylbutyrate," Hepatology 57(6):2171-2179 (2013).
Dixon, M. A. and Leonard, J.V., Intercurrent Illness In Inborn Errors of Intermediary Merabolism, 67 Archives of Disease in Childhood 1387 (1992).
Dover, G. et al, Induction of Fetal Hemoglobin Production in Subjects with Sickle Cell Anemia by Oral Sodium Phenylbutyrate, 54 Cancer Research 3494 (1994).
Endo, F. et al., Clinical Manifestations of Inborn Errors of the Urea Cycle and Related Metabolic Disorders During Childhood, 134 J. Nutrition 1605S (2004).
European Medicines Agency, Annex I: Summary of Product Characteristics for Ammonaps.
European Medicines Agency, European Public Assessment Report: Summary for the Public for Ammonaps (2009).
European Medicines Agency, Scientific Discussion for Ammonaps (2005).
European Medicines Agency, Scientific Discussion for Carbaglu (2004).
FDA Label for Ammonul®, sixteen pages. (Feb. 2005).
FDA Label for Carbaglu, seven pages. (Mar. 2010).
Feillet, F. and Leonard, J.V., Alternative Pathway Therapy for Urea Cycle Disorders, 21 J. Inher. Metab. Dis. 101-111 (1998).
Feoli-Fonseca, M. L., Sodium Benzoate Therapy in Children with Inborn Errors of Urea Synthesis: Effect on Carnitine Metabolism and Ammonia Nitrogen Removal, 57 Biochemical and Molecular Medicine 31 (1996).
Ferenci, P., et al., "Hepatic Encephalopathy-Definition, Nomenclature, Diagnosis, and Quantification: Final Report of the Working Party at the 11th World Congresses of Gastroenterology, Vienna, 1998," Hepatology 35:716-721 (2002).
Fernades, Saudubray, Bergne (editors), Inborn Metabolic Diseases Diagnosis and Treatment, 219-222 (3d ed. 2000).
Geraghty, M.T. and Brusilow, S.W., Disorders of the Urea Cycle, in Liver Disease in Children 827 (F.J. Suchy et al., eds. 2001).
Ghabril, M. et al., "Glycerol Phenylbutyrate in Patients with Cirrhosis and Episodic Hepatic Encephalopathy: A Pilot Study of Safety and Effect on Venous Ammonia Concentration," Clinical Pharmacology in Drug Development 2(3): 278-284 (2013).
Gilbert, J. et al., A Phase I Dose Escalation and Bioavailability Study of Oral Sodium Phenylbutyrate in Patients with Refractory Solid Tumor Malignancies, 7 Clin. Cancer Research 2292-2300 (2001).
Gore, S. et al., Impact of the Putative Differentiating Agent Sodium Phenylbutyrate on Myelodysplastic Syndromes and Acute Myeloid Leukemia, 7 Clin. Cancer Res. 2330 (2001).
Gropman, A.L. et al., Neurological Implications of Urea Cycle Disorders, 30 J. Inherit Metab Dis. 865 (2007).
Hassanein, T. I., et al., "Randomized Controlled Study of Extracorporeal Albumin Dialysis for Hepatic Encephalopathy in Advanced Cirrhosis," Hepatology 46:1853-1862 (2007).
Hassanein, T. I., et al., "Introduction to the Hepatic Encephalopathy Scoring Algorithm (HESA)," Dig. Dis. Sci. 53:529-538 (2008).
Hassanein, T., et al., "Performance of the Hepatic Encephalopathy Scoring Algorithm in a Clinical Trial of Patients With Cirrhosis and Severe Hepatic Encephalopathy," Am. J. Gastroenterol. 104:1392-1400 (2009).
Honda, S. et al., Successful Treatment of Severe Hyperammonemia Using Sodium Phenylacetate Power Prepared in Hospital Pharmacy, 25 Biol. Pharm. Bull. 1244 (2002).
International Search Report and Written Opinion for PCT/US2009/055256, mailed Dec. 30, 2009, 13 pages.
Inter Partes Review of U.S. Pat. No. 8,404,215.
Inter Partes Review of U.S. Pat. No. 8,642,012.
Kleppe, S. et al., Urea Cycle Disorders, 5 Current Treatment Options in Neurology 309-319 (2003).

(56) References Cited

OTHER PUBLICATIONS

Kubota, K. and Ishizaki, T., Dose-Dependent Pharmacokinetics of Benzoic Acid Following Oral Administration of Sodium Benzoate to Humans, 41 Eur. J. Clin. Pharmacol. 363 (1991).

Lea et al., "Butyramide and Monobutyrin: Growth Inhibitory and Differentiating Agents", Anticancer Res., 13: 145-150 (1993).

Lee, B. and Goss, J., Long-Term Correction of Urea Cycle Disorders, 138 J. Pediatrics S62 (2001).

Lee, B. et al., Considerations in the Difficult-to-Manage Urea Cycle Disorder Patient, 21 Crit. Care Clin. S19 (2005).

Lee, B. et al. (Aug. 2008). "Preliminary Data on Adult Patients with Urea Cycle Disorders (UCO) in an Open-Label, Switch-Over, Dose-Escalation Study Comparing a New Ammonia Scavenger, Glyceryl Tri (4-Phenylbutyrate) [HPN—100], to Buphenyl® (Sodium Phenylbutyrate [PBAj])," abstract presented at SSIEM 2008, Lisbon, Portugal, one page.

Lee, B., et al., "Optimizing Ammonia (NH3) Control in Urea Cycle Disorder (UCD) Patients: A Predictive Model," Oral Abstract Platform Presentations, Biochemical Genetics, Phoenix, AZ, Mar. 22, 2013.

Leonard, J.V., Urea Cycle Disorders, 7 Semin. Nenatol. 27 (2002).

Lizardi-Cervera, J. et al., Hepatic Encephalopathy: A Review, 2 Annals of Hepatology 122-120 (2003).

Maestri NE, et al., Prospective treatment of urea cycle disorders. J Paediatr 1991;119:923-928.

Maestri, N.E., et al., Long-Term Survival of Patients with Argininosuccinate Synthetase Deficiency, 127 J. Pediatrics 929 (1993).

Maestri, N.E., Long-Term Treatment of Girls with Ornithine Transcarbamylase Deficiency, 355 N. Engl. J. Med. 855 (1996).

Majeed, K., Hyperammonemia, eMedicine.com (Dec. 2001).

Matsuda, I., Hyperammonemia in Pediatric Clinics: A Review of Ornithine Transcarbamylase Deficiency (OTCD) Based on our Case Studies, 47 JMAJ 160 (2004).

Mizutani, N. et al., Hyperargininemia: Clinical Course and Treatment with Sodium Benzoate and Phenylacetic Acid, 5 Brain and Development 555 (1983).

Mokhtarani, M., et al., (2013) "Elevated Phenylacetic Acid Levels Do Not Correlate with Adverse Events in Patients with Urea Cycle Disorders o rHepatic Encephalopathy and Can Be Predicted Based on the Plasma PAA to PAGN Ratio," Mol Genet Metab 110(4):446-453.

Mokhtarani, M., et al., (2012) "Urinary Phenylacetylglutamine as Dosing Biomarker for Patients with Urea Cycle Disorders," Mol Genet Metab 107(3):308-314.

Montleone, JPR, et al., (2013) "Population Pharmacokinetic Modeling and Dosing Simulations of Nitrogen-Scavenging Compounds: Disposition of Glycerol Phenylbutyrate and Sodium Phenylbutyrate in Adult and Pediatric Patients with Urea Cycle Disorders," J. Clin. Pharmacol. 53(7): 699-710.

Munoz, S. J., "Hepatic Encephalopathy," Med. Clin. N. Am. 92:795-812 (2008).

Nassogne, M.C., Urea Cycle Defects: Management and Outcome, 28 J. Inherit. Metab. Dis. 407 (2005).

New England Consortium of Metabolic Programs, Acute Illness Protocol: Urea Cycle Disorders: The Infant/Child with Argininosuccinate Lyase Deficiency, adapted from Summar, M and Tuchman, M, Proceedings of a Consensus Conference for the Management of Patients with Urea Cycle Disorders, 138 J. Peds. Suppl. S6 (2001).

New England Consortium of Metabolic Programs, Acute Illness Protocol: Urea Cycle Disorders: The Infant/Child with Citrullinemia, adapted from Summar, M and Tuchman, M, Proceedings of a Consensus Conference for the Management of Patients with Urea Cycle Disorders, 138 J. Peds. Suppl. S6 (2001).

Newmark, H. L. and Young, W. C., Butyrate and Phenylacetate as Differentiating Agents: Practical Problems and Opportunities, 22 J. Cellular Biochemistry 247 (1995).

Ortiz, M., et al., "Development of a Clinical Hepatic Encephalopathy Staging Scale," Aliment Pharmacol Ther 26:859-867 (2007).

Par Pharmaceutical, Inc.'s Initial Invalidity Contentions and Non-Infringement Contentions For U.S. Pat. No. 8,404,215 and U.S. Pat. No. 8,642,012.

Parsons-Smith, B. G., et al., "The Electroencephalograph in Liver Disease," Lancet 273:867-871 (1957).

Phuphanich, S. et al., Oral Sodium Phenylbutyrate in Patients with Recurrent Malignant Gliomas: A Dose Escalation and Pharmacologic Study, Neuro-Oncology 177 (2005).

Praphanproj, V. et al., Three Cases of Intravenous Sodium Benzoate and Sodium Phenylacetate Toxicity Occurring in the Treatment of Acute Hyperammonemia, 23 J. Inherited Metabolic Disease 129 (2000).

Rockey, D. C., et al., "Randomized, Controlled, Double Blind Study of Glycerol Phenylbutyrate in Patients with Cirrhosis and Episodic Hepatic Encephalopathy," Hepatology 56:248(A) (2012).

Salam, M., et al., "Modified-Orientation Log to Assess Hepatic Encephalopathy," Aliment Pharmacol Ther. 35(8):913- 920 (2012).

Scottish Medicines Consortium, Carglumic Acid 200 mg Dispersible Tablets (Carbaglu®) No. 299/06 (Sep. 8, 2006).

Seakins, J.W.T., The Determination of Urinary Phenylacetylglutamine as Phenylacetic Acid: Studies on its Origin in Normal Subjects and Children with Cystic Fibrosis, 35 Clin. Chim. Acta. 121 (1971).

Search and Examination Report for British Application No. GB 0915545.8, dated Oct. 8, 2009, 5 pages.

Seiki et al., "Homogenous Pharmaceutical Emulsions Containing Nonsteriodal Analogesics and Inflammation Inhibitors" Chemical Abstract, vol. 116, No. 46308.

Sherwin, C. et al.,The Maximum Production of Glutamine by the Human Body as Measured by the Output of Phenylacetylglutamine, 37 J. Biol. Chem. 113 (1919).

Smith, W., et al., "Ammonia Control in Children Ages 2 Months through 5 Years with Urea Cycle Disorders: Comparison of Sodium Phenylbutyrate and Glycerol Phenylbutyrate," J Pediatr. 162(6):1228-1234.e1 (2013).

Summar, M., Current Strategies for the Management of Neonatal Urea Cycle Disorders, 138 J. Pediatrics S30 (2001).

Summar, M. et al., Unmasked Adult-Onset Urea Cycle Disorders in the Critical Care Setting, 21 Crit. Care Clin. S1 (2005).

The National Organization for Rare Disorders (2012). The Physician's Guide to Urea Cycle Disorders, at http://nordphysicianguides.org/wp-content/uploads/2012/02/NORD_Physician_Guide_to_Urea_Cycle_Disorders.pdf.

Todo, S. et al., Orthotopic Liver Transplantation for Urea Cycle Enzyme Deficiency, 15 Hepatology 419 (1992).

Tuchman, M., and Yudkoff, M., Blood Levels of Ammonia and Nitrogen Scavenging Amino Acids in Patients with Inherited Hyperammonemia, 66 Molecular Genetics and Metabolism 10-15 (1999).

United States Patent and Trademark Office, International Search Report and Written Opinion dated Jan. 16, 2015 for PCT/US14/58489.

United States Patent and Trademark Office, International Search Report and Written Opinion for PCT/US2014/060543 dated Jan. 23, 2015.

Vilstrup, H., et al., "Hepatic Encephalopathy in Chronic Liver Disease: 2014 Practice Guideline by the American Association for the Study of Liver Diseases and the European Association for the Study of the Liver," Hepatology 60 (2):715-735 (2014).

Walsh et al., Chemical Abstract vol. 112, No. 231744.

Walsh et al., The Journal of Biological Chemistry, vol. 265, No. 8, pp. 4374-4381 (1990), "sn-1,2-Diacylgylcerol Kinase of *Escherichia coli*".

Welbourne, T. et al., The Effect of Glutamine Administration on Urinary Ammonium Excretion in Normal Subjects and Patients with Renal Disease, 51 J. Clin. Investigation 1852 (1972).

Wilcken, B., Problems in the Management of Urea Cycle Disorders, 81 Molecular Genetics and Metabolism 85 (2004).

Wilson, C.J., et al., Plasma Glutamine and Ammonia Concentrations in Ornithine Carbamoyltransferase Deficiency and Citrullinaemia, 24 J. Inherited Metabolic Disease 691 (2001).

(56) References Cited

OTHER PUBLICATIONS

Wright, G., et al., Management of Hepatic Encephalopathy, 2011 International Journal of Hepatology 1 (2011).

Wright, P., Review: Nitrogen Excretion: Three End Products, Many Physiological Roles, 198 J. Experimental Biology 273 (1995).

Yajima, et al. Diurnal Fluctuations of Blood Ammonia Levels in Adult-Type Citrullinemia, 137 Tokohu J. Ex/Med, 213-220 (1982).

Yu, Ryan and Potter, Murray, Diagnosis of Urea Cycle Disorders in Adulthood: Late-Onset Carbamyl Phosphate Synthetase 1 Deficiency, 7 MUMJ 30 (2010).

Yudkoff, M. et al., In Vivo Nitrogen Metabolism in Ornithine Transcarbamylase Deficiency, 98 J. Clin. Invest. 2167 (1996).

Zeitlin, P., Novel Pharmacologic Therapies for Cystic Fibrosis, 103 J. Clinical Investigation 44/(1999).

\* cited by examiner

METHODS OF ADMINISTERING AND EVALUATING NITROGEN SCAVENGING DRUGS FOR THE TREATMENT OF HEPATIC ENCEPHALOPATHY

RELATED APPLICATIONS

The present application claims priority to U.S. Provisional Application No. 61/728,967, filed Nov. 21, 2012, and U.S. Provisional Application No. 61/759,292, filed Jan. 31, 2013, the disclosures of which are incorporated by reference herein in their entirety, including drawings.

BACKGROUND

Hepatic encephalopathy (HE) refers to a spectrum of neurologic signs and symptoms believed to result from increased blood ammonia levels, which frequently occur in subjects with cirrhosis or certain other types of liver disease. Subjects with HE typically show altered mental status ranging from subtle changes to coma, features similar to those in subjects with urea cycle disorders (UCDs).

Glycerol phenylbutyrate (glyceryl tri-[4-phenylbutyrate]) (HPN-100, GPB, GT4P, glycerol PBA), which is described in U.S. Pat. No. 5,968,979, is currently under development for treatment of HE. Like sodium PBA (NaPBA, approved in the United States as BUPHENYL® and in Europe as AMMONAPS®) and sodium benzoate, HPN-100 is a nitrogen scavenging agent. These drugs are often referred to as alternate pathway drugs because they provide the body with an alternate pathway to urea for excretion of waste nitrogen (Brusilow 1980; Brusilow 1991).

NaPBA is a phenylacetic acid (PAA) prodrug, while HPN-100 is a prodrug of PBA and a pre-prodrug of PAA. HPN-100 and NaPBA share the same general mechanism of action: PBA is converted to PAA via beta oxidation, and PAA is conjugated enzymatically with glutamine to form phenylacetylglutamine (PAGN), which is excreted in the urine. The structures of PBA, PAA, and PAGN are set forth below.

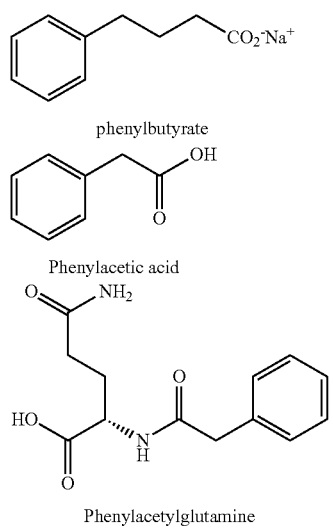

phenylbutyrate

Phenylacetic acid

Phenylacetylglutamine

The clinical benefit of NaPBA and HPN-100 with regard to nitrogen retention disorders such as HE derives from the ability of PAGN to effectively replace urea as a vehicle for waste nitrogen excretion and/or to reduce the need for urea synthesis (Brusilow 1991; Brusilow 1993). Because each glutamine contains two molecules of nitrogen, the body rids itself of two waste nitrogen atoms for every molecule of PAGN excreted in the urine (FIG. 1). Therefore, two equivalents of nitrogen are removed for each mole of PAA converted to PAGN. PAGN represents the predominant terminal metabolite, and one that is stoichiometrically related to waste nitrogen removal, a measure of efficacy in the case of nitrogen retention states. The difference between HPN-100 and NaPBA with respect to metabolism is that HPN-100 is a triglyceride and requires digestion, presumably by pancreatic lipases, to release PBA (McGuire 2010).

In contrast to NaPBA or HPN-100, sodium benzoate acts when benzoic acid is combined enzymatically with glycine to form hippuric acid. For each molecule of hippuric acid excreted in the urine, the body rids itself of one waste nitrogen atom.

Methods of determining an effective dosage of PAA prodrugs such as NaPBA or HPN-100 for a subject in need of treatment for a nitrogen retention disorder are described in WO09/1134460 and WO10/025303. While ammonia has long been suspected as important in the pathogenesis of HE, the data are largely correlative and it is only recently that an ammonia selective intervention has been shown to reduce the likelihood of HE events (Rockey 2012). Ammonia is not routinely monitored in patients with HE; rather, treatment is based on clinical assessment.

SUMMARY

Provided herein in certain embodiments are methods of treating hepatic encephalopathy in a subject in need thereof by administering a nitrogen scavenging drug at a dosage sufficient to maintain a fasting blood ammonia level at or below a specified threshold level with respect to the upper limit of normal for blood ammonia. In certain of these embodiments, the threshold level is 1.5 times the upper limit of normal for blood ammonia, and in certain embodiments the upper limit of normal for blood ammonia is 35 μmol/L. In certain embodiments, the nitrogen scavenging drug is HPN-100, PBA, NaPBA, sodium benzoate, or any combination thereof (i.e., any combination of two or more of HPN-100, PBA, NaPBA).

Provided herein in certain embodiments are methods of treating hepatic encephalopathy in a subject in need thereof by administering a first dosage of a nitrogen scavenging drug, measuring fasting blood ammonia level, and comparing the fasting blood ammonia level to the upper limit of normal for blood ammonia to determine whether to increase the dosage of the drug, wherein the dosage needs to be increased if the fasting blood ammonia level is at or above a specified threshold level with respect to the upper limit of normal. In certain of these embodiments, the threshold level is 1.5 times the upper limit of normal for blood ammonia, and in certain embodiments the upper limit of normal for blood ammonia is 35 μmol/L. In certain embodiments, these methods include an additional step of administering a second dosage of the drug based on the comparison of fasting blood ammonia level to the upper limit of normal for blood ammonia. In certain embodiments, the nitrogen scavenging drug is HPN-100, PBA, NaPBA, sodium benzoate, or any combination thereof (i.e., any combination of two or more of HPN-100, PBA, NaPBA).

Provided herein in certain embodiments are methods of treating hepatic encephalopathy in a subject in need thereof by measuring fasting blood ammonia level, comparing the fasting blood ammonia level to the upper limit of normal for blood ammonia, and administering a nitrogen scavenging drug if the fasting blood ammonia level is at or above a specified threshold level with respect to the upper limit of normal. In certain of these embodiments, the threshold level is 1.5 times the upper limit of normal for blood ammonia, and in certain embodiments the upper limit of normal for blood ammonia is 35 µmol/L. In certain embodiments, the nitrogen scavenging drug is HPN-100, PBA, NaPBA, sodium benzoate, or any combination thereof (i.e., any combination of two or more of HPN-100, PBA, NaPBA). In certain embodiments, the subject has previously received a first dosage of a nitrogen scavenging drug, and in certain of these embodiments the nitrogen scavenging drug is administered at a dosage greater than the first dosage if the fasting blood ammonia level is at or above the specified threshold level with respect to the upper limit of normal.

Provided herein in certain embodiments are methods of treating hepatic encephalopathy in a subject in need thereof who has previously been administered a first dosage of a nitrogen scavenging drug by measuring fasting blood ammonia level, comparing the fasting blood ammonia level to the upper limit of normal for blood ammonia, and administering a second dosage of the drug that is greater than the first dosage if the fasting blood ammonia level is at or above a specified threshold level with respect to the upper limit of normal. In certain of these embodiments, the threshold level is 1.5 times the upper limit of normal for blood ammonia, and in certain embodiments the upper limit of normal for blood ammonia is 35 µmol/L. In certain embodiments, the nitrogen scavenging drug is HPN-100, PBA, NaPBA, sodium benzoate, or any combination thereof (i.e., any combination of two or more of HPN-100, PBA, NaPBA).

Provided herein in certain embodiments are methods of optimally administering a nitrogen scavenging drug for the treatment of hepatic encephalopathy in a subject in need thereof that include a step of administering the nitrogen scavenging drug, wherein the dosage of the drug is adjusted to maintain a fasting blood ammonia at or below a specified threshold level with respect to the upper limit of normal for blood ammonia. In certain of these embodiments, the threshold level is 1.5 times the upper limit of normal for blood ammonia, and in certain embodiments the upper limit of normal for blood ammonia is 35 µmol/L. In certain embodiments, the nitrogen scavenging drug is HPN-100, PBA, NaPBA, sodium benzoate, or any combination thereof (i.e., any combination of two or more of HPN-100, PBA, NaPBA).

Provided herein in certain embodiments are methods of optimizing the dosage of a nitrogen scavenging drug for the treatment of hepatic encephalopathy in a subject in need thereof by administering a first dosage of a nitrogen scavenging drug, measuring fasting blood ammonia level, and comparing the fasting blood ammonia level to the upper limit of normal for blood ammonia to determine whether to increase the dosage of the drug, wherein the dosage needs to be increased if the fasting blood ammonia level is at or above a specified threshold level with respect to the upper limit of normal. In certain of these embodiments, the threshold level is 1.5 times the upper limit of normal for blood ammonia, and in certain embodiments the upper limit of normal for blood ammonia is 35 µmol/L. In certain embodiments, these methods include an additional step of administering a second dosage of the drug based on the comparison of fasting blood ammonia level to the upper limit of normal for blood ammonia. In certain embodiments, the nitrogen scavenging drug is HPN-100, PBA, NaPBA, sodium benzoate, or any combination thereof (i.e., any combination of two or more of HPN-100, PBA, NaPBA).

Provided herein in certain embodiments are methods of adjusting the dosage of a nitrogen scavenging drug for the treatment of hepatic encephalopathy in a subject in need thereof by administering a first dosage of a nitrogen scavenging drug, measuring fasting blood ammonia level, and determining whether the drug dosage needs to be adjusted based on the fasting blood ammonia level, wherein a fasting blood ammonia level at or above a specified threshold level with respect to the upper limit of normal for blood ammonia indicates that the dosage needs to be increased. In certain of these embodiments, the threshold level is 1.5 times the upper limit of normal for blood ammonia, and in certain embodiments the upper limit of normal for blood ammonia is 35 µmol/L. In certain embodiments, these methods include an additional step of administering a second dosage of the drug based on the comparison of fasting blood ammonia level to the upper limit of normal for blood ammonia. In certain embodiments, the nitrogen scavenging drug is HPN-100, PBA, NaPBA, sodium benzoate, or any combination thereof (i.e., any combination of two or more of HPN-100, PBA, NaPBA).

Provided herein in certain embodiments are methods of treating hepatic encephalopathy in a subject in need thereof by determining a target urinary phenylacetyl glutamine output, calculating an effective initial dosage of a PAA prodrug to achieve the target urinary phenylacetyl glutamine output based on a mean conversion of PAA prodrug to urinary phenylacetyl glutamine of 52% to 63%, and administering the effective initial dosage of PAA prodrug to the subject. In certain embodiments, the PAA prodrug is HPN-100, PBA, or NaPBA.

Provided herein in certain embodiments are methods of administering a PAA prodrug for the treatment of hepatic encephalopathy in a subject in need thereof by administering a first dosage of the PAA prodrug, determining urinary phenylacetyl glutamine output following administration of the first dosage, determining an effective dosage of the PAA prodrug based on the urinary phenylacetyl glutamine output, wherein the effective dosage is based on a mean conversion of PAA prodrug to urinary PAGN of 52% to 63%, and administering the effective dosage to the subject.

DETAILED DESCRIPTION

Figure 1:
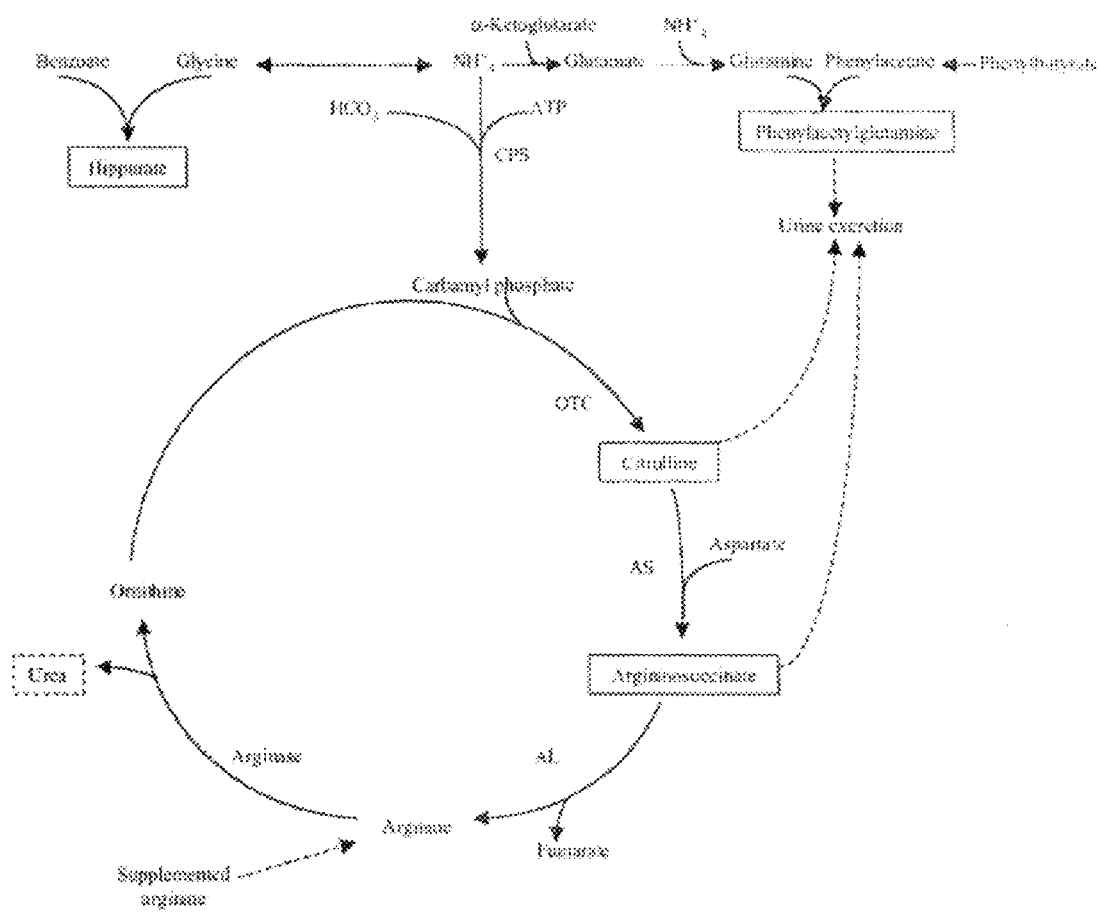
FIG. 1: The urea cycle and how certain nitrogen-scavenging drugs may assist in elimination of excessive ammonia.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

In subjects with HE, the desired effect of treatment with a nitrogen scavenging drug is prevention of HE events or reduction of the frequency of HE events and their associated cost and morbidity. The assessment of treatment effect and interpretation of ammonia levels is confounded by the fact that individual ammonia values vary several-fold over the course of a day and are impacted by timing of the blood draw in relation to the last meal and dose of drug (see, e.g., Lee 2010; Lichter-Konecki 2011; Diaz 2011, Ghabril 2012).

A random ammonia value obtained during an outpatient visit may fail to provide a reliable measure of a subject's status and the drug effect. For example, basing treatment on a blood sample taken after eating a meal might overestimate average daily ammonia level and result in overtreatment. Conversely, basing treatment on a blood sample taken after drug administration might underestimate average daily ammonia level and result in undertreatment. Furthermore, subjects may not exhibit dramatically increased ammonia levels between HE events, and assessment of ammonia level at the time of an HE event is not always possible. A more accurate view of daily ammonia level could be obtained by multiple blood draws in a controlled setting over an extended period of time. Although this is currently done in clinical trials, it is clinically impractical.

As set forth in the examples section below, the relationship between fasting ammonia levels and the likelihood of patients experiencing an HE event was evaluated in subjects with cirrhosis and HE. It was found that increased fasting ammonia levels correlated strongly with the likelihood of experiencing an HE event. Surprisingly, the relationship between ammonia levels and HE events was non-linear, and there was a step up in HE event risk at a fasting ammonia level of around 1.5 times the upper limit of normal (ULN) rather than at the ULN. Based on these results, a comparison of fasting ammonia levels to a specified threshold or target range with respect to the ULN for blood ammonia represents a novel, clinically useful, and practical predictor of HE event risk. The present application provides practical applications of this finding in the form of methods and kits for treating HE, optimally administering a nitrogen scavenging drug for the treatment of HE, adjusting and optimizing the dosage of a nitrogen scavenging drug for the treatment of HE, evaluating the efficacy of a nitrogen scavenging drug for the treatment of HE, determining whether to administer a nitrogen scavenging drug for the treatment of HE, predicting the likelihood or risk of an HE event, evaluating and monitoring ammonia exposure, and other related embodiments.

Provided herein are threshold levels and target ranges for fasting blood ammonia upon which an effective dosage of a nitrogen scavenging drug for the treatment of HE can be based. An effective dosage of a nitrogen scavenging drug as used herein refers to a dosage that results in a fasting blood ammonia level falling at or below a specified threshold level or within a specified target range after one or more administrations. In certain embodiments, the effective dosage results in a fasting blood ammonia level falling at or below a specified threshold level or within a specified target range after multiple administrations, and in certain of these embodiments the effective dosage results in a fasting blood ammonia level falling at or below a specified threshold level or within a specified target range after the drug has reached steady state. In certain embodiments, steady state for a particular dosage of a nitrogen scavenging drug is reached at around three days after the initial administration of that dosage. In other embodiments, steady state may be reached at two, four, or five days after the initial administration.

Threshold levels and target ranges for fasting blood ammonia are based on the ULN for blood ammonia. In certain embodiments, a specified target range for fasting blood ammonia is $<1.2$, $\leq 1.2$, $<1.3$, $\leq 1.3$, $<1.4$, $\leq 1.4$, $<1.5$, $\leq 1.5$, $<1.6$, $\leq 1.6$, $<1.7$, $\leq 1.7$, $<1.8$, $\leq 1.8$, $<1.9$, $\leq 1.9$, $<2.0$, or $\leq 2.0$ times the ULN for blood ammonia. In certain of these embodiments, the specified target range is $<1.5$ or $\leq 1.5$ times the ULN for blood ammonia. In other embodiments, a specified target range for fasting blood ammonia is 0.1 to 1.5, 0.5 to 1.5, 0.7 to 1.3, 0.8 to 1.2, or 1 to 1.5 times the ULN for blood ammonia. In certain embodiments, a specified threshold level for fasting blood ammonia is 1.2, 1.3, 1.4, 1.5, 1.6, 1.7, 1.8, 1.9, or 2.0 times the ULN for blood ammonia. In certain of these embodiments, the specified threshold level is 1.5 times the ULN for blood ammonia. In certain embodiments, a fasting blood ammonia level that is at or above the specified threshold level or above the specified target range indicates that a subject needs to be administered a nitrogen scavenging drug or, where the subject has received a nitrogen scavenging drug previously, that the subject needs to be administered a different nitrogen scavenging drug or a higher dosage of the original nitrogen scavenging drug. Similarly, in certain embodiments a fasting blood ammonia level that is at or below the specified threshold level or within the specified target range indicates that the subject does not need to be administered a nitrogen scavenging drug or, where the subject has received a nitrogen scavenging drug previously, that the subject should continue to be administered the same nitrogen scavenging drug and/or the same dosage. In certain embodiments, the optimal range for fasting blood ammonia includes the specified threshold level. In these embodiments, a fasting blood ammonia level at or below the specified threshold level is considered acceptable or optimal. For example, where the specified threshold level is 1.5, nitrogen scavenging drug administration may be started or increased if the fasting blood ammonia level is above 1.5. In other embodiments, the optimal range for fasting blood ammonia does not include the specified threshold level. In these embodiments, only a fasting blood ammonia level below the specified threshold level is considered acceptable or optimal. For example, where the specified threshold level is 1.5, nitrogen scavenging drug administration may be started or increased if a subject exhibits a fasting blood ammonia level at or above 1.5. An effective dosage of a nitrogen scavenging drug may be an initial dosage, subsequent/maintenance dosage, improved dosage, or a dosage determined in combination with other factors. In certain embodiments, the effective dosage may be the same as or different than an initial dosage. In other embodiments, the effective dosage may be higher or lower than an initial dosage.

Provided herein in certain embodiments are methods of treating HE in a subject in need thereof. The terms "treat," "treating," or "treatment" as used herein with regard to HE may refer to preventing HE events, reducing the number or frequency of HE events, decreasing the likelihood of experiencing an HE event, preventing, delaying, reducing, or ending symptoms associated with HE or HE events, or some combination thereof.

Overt HE events are often defined in the art as West Haven grade ≥2, typically manifested by confusion to time, place, person and/or somnolence and even coma. In addition, a West Haven grade 1 and an increase in asterixis scales for patients who are West Haven grade 0 when in remission is considered clinically significant. As used herein, the "HE event" refers to a West Haven Grade 2 or above or (2) a West Haven Grade 1 AND an asterixis grade increase of 1, if the baseline West Haven was 0.

A "subject in need thereof" as used herein refers to a human subject having HE, suspected of having HE, deemed at risk for developing HE based on one or more genetic or environmental factors, currently or previously experiencing an HE event, or deemed at risk of experiencing a future HE event.

In certain embodiments, the methods of treating HE provided herein comprise administering a nitrogen scavenging drug at a dosage sufficient to drop a subject's fasting blood ammonia level to or below a specified threshold level or to within a specified target range with respect to the ULN for blood ammonia, or to maintain the subject's fasting blood ammonia level at or below the specified threshold level or within the specified target range for a specific period of time (e.g., 2 days, 4 days, 1 week, 1 month, or indefinitely). For example, the drug may be administered at a dosage sufficient to maintain a subject's fasting blood ammonia level at or below a specified threshold level of 1.5 times the ULN, or at a dosage sufficient to maintain the subject's fasting blood ammonia level within a specified target range of 1 to 1.5, between 1 and 1.5, <1.5, or ≤1.5 times the ULN. In certain embodiments, administration of the nitrogen scavenging drug at a dosage sufficient to maintain a fasting blood ammonia level at or below a specified threshold level or within a specified target range with respect to the ULN for blood ammonia decreases the likelihood of the subject experiencing an HE event.

In certain embodiments, the methods of treating HE provided herein comprise (a) measuring a fasting blood ammonia level, (b) comparing the fasting blood ammonia level to the ULN for blood ammonia to determine whether to administer a nitrogen scavenging drug, and (c) administering a nitrogen scavenging drug if the fasting blood ammonia level is at or above a specified threshold level or above a specified target range with respect to the ULN. In certain embodiments, the specified threshold level is 1.5 times the ULN. In certain embodiments, the specified target range is 1 to 1.5, between 1 and 1.5, <1.5, or ≤1.5 times the ULN. In certain embodiments, administration of the nitrogen scavenging drug decreases the likelihood of the subject experiencing an HE event. In certain embodiments, the steps are repeated until a fasting blood ammonia level at or below the threshold level or within the target range is reached or maintained. In those embodiments where the steps are repeated, subsequent dosages may be the same as or different than the first dosage. For example, a second dosage may be administered that is greater than the first dosage if the first dosage was insufficient to lower fasting blood ammonia level to at or below the threshold level or to within the target range.

In certain embodiments, the methods of treating HE provided herein comprise (a) administering a first dosage of a nitrogen scavenging drug, (b) measuring a fasting blood ammonia level, and (c) comparing the fasting blood ammonia level to the ULN for blood ammonia to determine whether to increase the dosage of the nitrogen scavenging drug. In these embodiments, the dosage needs to be increased if the fasting blood ammonia level is at or above a specified threshold level or above a specified target range with respect to the ULN. In certain of these embodiments, these methods include an additional step of administering a second dosage of the drug greater than the first dosage based on the comparison in step (c). If the fasting blood ammonia level is at or below the specified threshold level or within the specified target range, on the other hand, the second dosage may be the same as or less than the first dosage. In certain embodiments, these steps may be repeated, with the subject receiving increasing dosages of nitrogen scavenging drug until a fasting blood ammonia level at or below the specified threshold or within target range is reached or maintained. For example, in certain embodiments fasting blood ammonia level may be measured after administration of the second dosage, and if the fasting blood ammonia level is at or above the specified threshold level or above the target range with respect to the ULN, a third dosage may be administered that is greater than the second dosage. In certain embodiments, the specified threshold level is 1.5 times the ULN. In certain embodiments, the specified target range is 1 to 1.5, between 1 and 1.5, <1.5, or ≤1.5 times the ULN. In certain embodiments, administration of the second, third, or subsequent dosage of the drug decreases the likelihood of the subject experiencing an HE event.

In certain embodiments, the methods of treating HE provided herein are directed to treatment of subjects who have previously received a first dosage of a nitrogen scavenging drug. In certain of these embodiments, the methods comprise (a) measuring a fasting blood ammonia level, (b) comparing the fasting blood ammonia level to the ULN for blood ammonia, and (c) administering a second dosage of the drug that is greater than the first dosage if the fasting blood ammonia level is at or above a specified threshold level or above a target range with respect to the ULN. If the fasting blood ammonia level is at or below the specified threshold level or within the specified target range, on the other hand, the second dosage may be the same as or less than the first dosage. In certain embodiments, these steps may be repeated. For example, in certain embodiments fasting blood ammonia level may be measured after administration of the second dosage, and if the fasting blood ammonia level is at or above the specified threshold level or above the target range with respect to the ULN, a third dosage may be administered that is greater than the second dosage. This process may be repeated until the subject exhibits a fasting ammonia level at or below the specified threshold level or within the specified target range. In certain embodiments, the specified threshold level is 1.5 times the ULN. In certain embodiments, the specified target range is 1 to 1.5, between 1 and 1.5, <1.5, or ≤1.5 times the ULN. In certain embodiments, administration of the second, third, or subsequent dosage of the nitrogen scavenging drug decreases the likelihood of the subject experiencing an HE event.

Provided herein in certain embodiments are methods of optimally administering a nitrogen scavenging drug to a subject in need thereof for treatment of HE. In certain embodiments, these methods comprise administering the nitrogen scavenging drug at a dosage sufficient to lower a subject's fasting blood ammonia to or below a specified threshold level or to within a specified target range with respect to the ULN for blood ammonia, or to maintain the subject's fasting blood ammonia level at or below the threshold level or within the target range. For example, in certain embodiments the drug may be administered at a dosage sufficient to maintain a subject's fasting blood ammonia level below a specified threshold level of 1.5 times the ULN, or within a specified target range of 1 to 1.5, between 1 and 1.5, <1.5, or ≤1.5 times the ULN. In certain embodiments, administration of the nitrogen scavenging drug decreases the likelihood of the subject experiencing an HE event.

In certain embodiments, the methods of optimally administering a nitrogen scavenging drug for the treatment of HE provided herein comprise (a) measuring a fasting blood ammonia level, (b) comparing the fasting blood ammonia level to the ULN for blood ammonia to determine whether to administer a nitrogen scavenging drug, and (c) administering a first dosage of a nitrogen scavenging drug if the fasting blood ammonia level is at or above a specified threshold level or above a specified target range with respect to the ULN. In certain embodiments, the specified threshold level is 1.5 times the ULN. In certain embodiments, the specified target range is 1 to 1.5, between 1 and 1.5, <1.5, or ≤1.5 times the ULN. In certain embodiments, the steps are repeated until a fasting blood ammonia level at or below the threshold level or within the target range is reached or maintained. In those embodiments where the steps are repeated, the dosage of the nitrogen scavenging drug may be adjusted with each subsequent administration in order to obtain a fasting blood ammonia level at or below the threshold level or within the target range.

In certain embodiments, the methods of optimally administering a nitrogen scavenging drug for the treatment of HE provided herein comprise (a) administering a first dosage of a nitrogen scavenging drug, (b) measuring a fasting blood ammonia level, and (c) comparing the fasting blood ammonia level to the ULN for blood ammonia to determine whether to increase the dosage of the drug, wherein the dosage needs to be increased if the fasting blood ammonia level is at or above a specified threshold level or above a specified target range with respect to the ULN. In certain embodiments, these methods include an additional step of administering a second dosage of the drug based on the comparison step (c). If the fasting blood ammonia level is at or below the specified threshold level or within the specified target range, on the other hand, the second dosage may be the same as or less than the first dosage. In certain embodiments, these steps may be repeated, with the subject receiving increasing dosages of nitrogen scavenging drug until a fasting blood ammonia level at or below the specified threshold or within the specified target range is reached or maintained. For example, in certain embodiments fasting blood ammonia level may be measured after administration of the second dosage, and if the fasting blood ammonia level is at or above the specified threshold level or above the specified target range with respect to the ULN, a third dosage may be administered that is greater than the second dosage. In certain embodiments, the specified threshold level is 1.5 times the ULN. In certain embodiments, the specified target range is 1 to 1.5, between 1 and 1.5, <1.5, or ≤1.5 times the ULN. In certain embodiments, administration of the nitrogen scavenging drug decreases the likelihood of the subject experiencing an HE event.

In certain embodiments, the methods of optimally administering a nitrogen scavenging drug for the treatment of HE provided herein are directed to subjects who have previously received a first dosage of a nitrogen scavenging drug. In certain of these embodiments, the methods comprise (a) measuring a fasting blood ammonia level, (b) comparing the fasting blood ammonia level to the ULN for blood ammonia, and (c) administering a second dosage of the drug that is greater than the first dosage if the fasting blood ammonia level is at or above a specified threshold level or above a specified target range with respect to the ULN. If the fasting blood ammonia level is at or below the specified threshold level or within the specified target range, on the other hand, the second dosage may be the same as or less than the first dosage. In certain embodiments, these steps may be repeated. For example, in certain embodiments fasting blood ammonia level may be measured after administration of the second dosage, and if the fasting blood ammonia level is at or above the specified threshold level or above the specified target range with respect to the ULN, a third dosage may be administered that is greater than the second dosage. This process may be repeated until the subject exhibits a fasting ammonia level at or below the specified threshold level or within the specified target range. In certain embodiments, the specified threshold level is 1.5 times the ULN. In certain embodiments, the specified target range is 1 to 1.5, between 1 and 1.5, <1.5, or ≤1.5 times the ULN. In certain embodiments, administration of the second, third, or subsequent dosage of the nitrogen scavenging drug decreases the likelihood of the subject experiencing an HE event.

Provided herein in certain embodiments are methods of adjusting the dosage of a nitrogen scavenging drug for the treatment of HE in a subject in need thereof. In certain embodiments, these methods comprise adjusting the dosage of a nitrogen scavenging drug to lower a subject's fasting blood ammonia to or below a specified threshold level or to within a specified target range with respect to the ULN for blood ammonia, or to maintain the subject's fasting blood ammonia level at or below the threshold level or within the specified target range. For example, the dosage may be adjusted to a dosage sufficient to maintain a subject's fasting blood ammonia level at or below a specified threshold level of 1.5 times the ULN or within a specified target range of 1 to 1.5, between 1 and 1.5, <1.5, or ≤1.5 times the ULN. In certain embodiments, administration of the adjusted dosage of nitrogen scavenging drug decreases the likelihood of the subject experiencing an HE event.

In certain embodiments, the methods of adjusting the dosage of a nitrogen scavenging drug for the treatment of HE provided herein comprise (a) administering a first dosage of a nitrogen scavenging drug, (b) measuring a fasting blood ammonia level, and (c) determining whether the drug dosage needs to be adjusted based on the fasting blood ammonia level, wherein a fasting blood ammonia level at or above a specified threshold level or above a specified target range with respect to the ULN for blood ammonia indicates that the dosage needs to be increased. In certain embodiments, these methods include an additional step of administering an adjusted second dosage of the drug based on the comparison step (c). In certain embodiments, if the fasting blood ammonia level in step (b) is at or below the specified threshold level or within the specified target range, the adjusted second dosage may be the same as or less than the first dosage. In certain embodiments, the steps may be repeated, with the subject receiving increasing dosages of nitrogen scavenging drug until a fasting blood ammonia level at or below the specified threshold level or within the specified target range is reached or maintained. For example, in certain embodiments fasting blood ammonia level may be measured after administration of the second dosage, and if the fasting blood ammonia level is at or above the specified threshold level or above the specified target range with respect to the ULN, a third dosage may be administered that is greater than the second dosage. In certain embodiments, the specified threshold level is 1.5 times the ULN. In certain embodiments, the specified target range is 1 to 1.5, between 1 and 1.5, <1.5, or ≤1.5 times the ULN. In certain embodiments, administration of the nitrogen scavenging drug decreases the likelihood of the subject experiencing an HE event.

In certain embodiments, the methods of adjusting the dosage of a nitrogen scavenging drug for the treatment of HE provided herein are directed to subjects who have previously received a first dosage of a nitrogen scavenging drug. In certain of these embodiments, the methods comprise (a) measuring a fasting blood ammonia level and (b) determining whether the drug dosage needs to be adjusted based on the fasting blood ammonia level, wherein a fasting blood ammonia level at or above a specified threshold level or above a specified target range with respect to the ULN for blood ammonia indicates that the dosage needs to be increased. In certain embodiments, these methods include an additional step of administering an adjusted second dosage of the drug based on the comparison step (c). In certain embodiments, if the fasting blood ammonia level in step (a) is at or below the specified threshold level or within the specified target range, the adjusted second dosage may be the same as or less than the first dosage. In certain embodiments, the steps may be repeated, with the subject receiving increasing dosages of nitrogen scavenging drug until a fasting blood ammonia level at or below the specified threshold level or within the specified target range is reached or maintained. For example, in certain embodiments fasting blood ammonia level may be measured after administration of the second dosage, and if the fasting blood ammonia level is at or above the specified threshold level with respect to the ULN, a third dosage may be administered that is greater than the second dosage. In certain embodiments, the specified threshold level is 1.5 times the ULN. In certain embodiments, the specified target range is 1 to 1.5, between 1 and 1.5, <1.5, or ≤1.5 times the ULN. In certain embodiments, administration of the nitrogen scavenging drug decreases the likelihood of the subject experiencing an HE event.

Provided herein in certain embodiments are methods of evaluating the efficacy of a nitrogen scavenging drug for treatment of HE in a subject in need thereof. In certain embodiments, these methods comprise (a) measuring a fasting blood ammonia level in a subject who has been administered a nitrogen scavenging drug and (b) comparing the fasting blood ammonia level to the ULN for blood ammonia, wherein a fasting blood ammonia level at or above a specified threshold level or above a specified target range with respect to the ULN for blood ammonia indicates the nitrogen scavenging drug has not been fully effective. In certain embodiments, these methods comprise the additional step of administering an increased dosage of the nitrogen scavenging drug or administering a second nitrogen scavenging drug in lieu of or in addition to the original nitrogen scavenging drug. In certain embodiments, the specified threshold level is 1.5 times the ULN. In certain embodiments, the specified target range is 1 to 1.5, between 1 and 1.5, <1.5, or ≤1.5 times the ULN.

Provided herein in certain embodiments are methods of determining whether to administer a nitrogen scavenging drug for treatment of HE to a subject in need thereof comprising (a) measuring a fasting blood ammonia level and (b) comparing the fasting blood ammonia level to a specified threshold level or a specified target range with respect to the ULN for blood ammonia, wherein a fasting blood ammonia level at or above the specified threshold level or above the specified target range indicates that a nitrogen scavenging drug should be administered to the subject. In certain embodiments, these methods further comprise administering the nitrogen scavenging drug. In certain embodiments, the specified threshold level is 1.5 times the ULN. In certain embodiments, the specified target range is 1 to 1.5, between 1 and 1.5, <1.5, or ≤1.5 times the ULN. In certain embodiments, administration of the nitrogen scavenging drug decreases the likelihood of the subject experiencing an HE event.

Provided herein in certain embodiments are methods of determining whether to administer a second nitrogen scavenging drug for treatment of HE to a subject in need thereof who has previously been administered a first nitrogen scavenging drug comprising (a) measuring a fasting blood ammonia level after administration of the first nitrogen scavenging drug and (b) comparing the fasting blood ammonia level to a specified threshold level or specified target range with respect to the ULN for blood ammonia, wherein a fasting blood ammonia level at or above the specified threshold level or above the specified target range indicates the need to administer a second nitrogen scavenging drug. In certain embodiments, these methods further comprise administering the second nitrogen scavenging drug. In certain of these embodiments, the second nitrogen scavenging drug is administered in lieu of the first nitrogen scavenging drug. In other embodiments, the second nitrogen scavenging drug is administered in combination with the first nitrogen scavenging drug, either sequentially or simultaneously. In certain embodiments, the specified threshold level is 1.5 times the ULN. In certain embodiments, the specified target range is 1 to 1.5, between 1 and 1.5, <1.5, or ≤1.5 times the ULN. In certain embodiments, administration of the second nitrogen scavenging drug decreases the likelihood of the subject experiencing an HE event.

Provided herein in certain embodiments are methods of using fasting blood ammonia level to predict the likelihood and/or severity of future HE events. In certain of these embodiments, a subject is classified as more likely to experience an HE event or more likely to experience a severe HE event if the subject exhibits a fasting blood ammonia level at or above a specified threshold level or above a specified target range with respect to the ULN for blood ammonia. Similarly, in certain embodiments, a subject is classified as less likely to experience an HE event or less likely to experience a severe HE event if the subject exhibits a fasting blood ammonia level at or below a specified threshold level or within a specified target range with respect to the ULN for blood ammonia. In certain embodiments, the specified threshold level is 1.5 times the ULN. In certain embodiments, the specified target range is 1 to 1.5, between 1 and 1.5, <1.5, or ≤1.5 times the ULN. In certain embodiments, a subject's risk of experiencing an HE event increases the higher the fasting blood ammonia level rises above the specified threshold level or specified target range. For example, where the specified threshold level is 1.5, a subject with a fasting blood ammonia level of 2.0 times the ULN for blood ammonia may be classified as more likely to experience an HE event than a subject with a fasting blood ammonia level 1.6 times the ULN. Similarly, in certain embodiments, the likely severity of a future HE event increases the higher the fasting blood ammonia level rises above the specified threshold value or specified target range. For example, where the specified threshold level is 1.5, a subject with a fasting blood ammonia level of 2.0 times the ULN for blood ammonia may be expected to experience more severe HE events than a subject with a fasting blood ammonia level 1.6 times the ULN. In certain embodiments, these methods further comprise taking steps to reduce the likelihood that the subject will experience an HE event, and in certain of these embodiments the methods comprise administering a nitrogen scavenging drug or an increased dosage of a nitrogen scavenging. In certain of these embodiments, the nitrogen scavenging drug is administered at a dosage sufficient to drop a subject's fasting blood ammonia level to or below a specified threshold level or to within a specified target range with respect to the ULN for blood ammonia, or to maintain the subject's fasting blood ammonia level at or below the specified threshold level or within the specified target range for a specific period of time.

The ULN for blood ammonia typically represents the highest level in the range of normal values, which may be influenced by a variety of factors such as the assay method, types of regents, standard reference samples used, and specifications and calibration of equipment used to perform the measurement. In certain embodiments of the methods disclosed herein, the ULN for blood ammonia is determined for a subject individually. In other embodiments, the ULN for blood ammonia may be based on measurements obtained across a set of subjects (e.g., healthy subjects or subjects with HE). In certain embodiments, the ULN for blood ammonia may represent a standard reference value disclosed in the art, such as a mean ULN developed across a particular subset of subjects. In other embodiments, the ULN for blood ammonia may represent a standard measurement that has been developed by a particular entity that performs blood draws and/or blood evaluations, such as a particular clinical laboratory. In certain embodiments, the ULN is a standard reference value utilized by the same entity that measures the fasting blood ammonia level. In these embodiments, one skilled in the art will recognize that the units of ammonia measurement may also vary from lab to lab (e.g., µg/mL or µmol/L), emphasizing the importance of interpreting the subject's ammonia levels relative to the ULN at the laboratory in which the measurement was performed. In certain embodiments, the ULN for blood ammonia may be about 12 to 70 µmol/L. In certain of these embodiments, the ULN for blood ammonia may be about 11 to 64 µmol/L, 20 to 50 µmol/L, 30 to 40 µmol/L, 32 to 38 µmol/L, or 34 to 36 µmol/L, and in certain of these embodiments the ULN for blood ammonia is about 35 µmol/L. In certain embodiments, the ULN for blood ammonia may be about 20 to 120 µg/dL. In certain of these embodiments, the ULN for blood ammonia may be about 50 to 65 µg/dL, 55 to 63 µg/dL, or 57 to 61 µg/dL, and in certain of these embodiments the ULN for blood ammonia is about 59 µg/dL.

A nitrogen scavenging drug as used herein refers to any drug that decreases blood nitrogen and/or ammonia levels. In certain embodiments, a nitrogen scavenging drug may remove nitrogen in the form of PAGN, and in certain of these embodiments the nitrogen scavenging drug may be an orally administrable drug that contains or is metabolized to PAA. For example, a nitrogen scavenging drug may be a PAA prodrug such as PBA or HPN-100, a pharmaceutically acceptable salt of PBA such as NaPBA, or a pharmaceutically acceptable ester, acid, or derivative of a PAA prodrug. In other embodiments, a nitrogen scavenging drug may remove nitrogen via hippuric acid. In certain of these embodiments, a nitrogen scavenging drug may be benzoic acid, a pharmaceutically acceptable salt of benzoic acid such as sodium benzoate, or a pharmaceutically acceptable ester, acid, or derivative of benzoic acid.

Increasing the dosage of a nitrogen scavenging drug may refer to increasing the amount of drug per administration (e.g., an increase from a 3 mL dosage to a 6 mL dosage), increasing the number of administrations of the drug (e.g., an increase from once-a-day dosing to twice- or three-times-a-day), or any combination thereof.

In certain embodiments, a subject that has previously been administered a nitrogen scavenging drug has been administered the drug for a duration of time sufficient to reach steady state. Similarly, in those methods where fasting blood ammonia level is measured following a first, second, third, or subsequent dosage of nitrogen scavenging drug, the measurement may be carried out after the drug has had sufficient time to reach steady state at that dosage. For example, the subject may have been administered the drug over a period of about 2 to 7 days, 1 week to 2 weeks, 2 weeks to 4 weeks, 4 weeks to 8 weeks, 8 weeks to 16 weeks, or longer than 16 weeks.

In certain embodiments of the methods disclosed herein, the fasting period for obtaining a fasting blood ammonia level is overnight. In certain embodiments, the fasting period is 4 hours or more, 5 hours or more, 6 hours or more, 7 hours or more, 8 hours or more, 9 hours or more, 10 hours or more, 11 hours or more, or 12 hours or more, and in certain embodiments the fasting period is 4 to 8 hours, 6 to 8 hours, or 8 to 12 hours. During the fasting period, the subject preferably does not ingest any food. In certain embodiments, the subject may also refrain from ingesting certain non-food substances during the fasting period. For example, in certain embodiments the subject does not ingest any supplements and/or nitrogen scavenging drugs during the fasting period. In certain of these embodiments, the subject may nonetheless ingest one or more drugs other than nitrogen scavenging drugs during the fasting period. In certain embodiments, the subject does not ingest any high calorie liquids during the fasting period. In certain of these embodiments, the subject does not ingest any liquids other than water during the fasting period. In other embodiments, the subject may ingest small amounts of low calorie beverages, such as tea, coffee, or diluted juices.

In certain embodiments of the methods disclosed herein, blood samples used for measuring fasting blood ammonia levels and/or ULN blood ammonias are venous blood samples. In certain embodiments, a blood sample is a plasma blood sample. Any methods known in the art may be used to obtain a plasma blood sample. For example, blood from a subject may be drawn into a tube containing heparin or ethylenediaminetetraacetic acid (EDTA). In certain embodiments, the sample can be placed on ice and centrifuged to obtain plasma within 15 minutes of collection, stored at 2 to 8° C. (36 to 46° F.) and analyzed within 3 hours of collection. In other embodiments, the blood plasma sample is snap frozen, stored at ≤−18° C. (≤0° F.) and analyzed at a later time. For example, the sample may be analyzed at 0 to 12 hours, 12 to 24 hours, 24 to 48, 48 to 96 hours after freezing, or within any other timeframe over which the sample has demonstrated stability. In certain embodiments, blood samples are taken in a laboratory or hospital setting. In certain embodiments, a single fasting blood sample is used to measure fasting blood ammonia level. However, in other embodiments, multiple fasting blood samples may be obtained. In certain embodiments, a subject's blood ammonia level may be monitored throughout the day. Further, in certain embodiments, the methods disclosed herein comprise an additional step of obtaining one or more blood samples from a subject prior to or after measuring fasting blood ammonia level.

In certain embodiments, a blood sample is analyzed immediately after collection. In other embodiments, the blood sample is stored for some period between collection and analysis. In these embodiments, the sample may be stored for less than 1 hour, 1 hour to 6 hours, 1 hour to 12 hours, 1 hour to 24 hours, or 1 hour to 48 hours. In certain of these embodiments, the blood sample is stored at a temperature between 0 to 15° C., such as 2 to 8° C. In other embodiments, the blood sample is stored below 0° C. or below −18° C.

Measurement of ammonia levels in a fasting blood sample may be carried out using any technique known in the art. For example, ammonia levels may be measured using a colorimetric reaction or an enzymatic reaction. In certain embodiments, a colorimetric reaction may involve the use of bromophenol blue as an ammonia indicator. In these embodiments, ammonia may react with bromophenol blue to yield a blue dye. In certain embodiments, an enzymatic reaction may involve glutamate dehydrogenase catalyzing the reductive amination of 2-oxoglutarate with $NH^{4+}$ and NADPH to form glutamate and $NADP^+$. The formation of $NADP^+$ formed is directly proportional to the amount of ammonia present in the blood sample. Therefore, the concentration of ammonia is measured based on a decrease in absorbance.

As further set forth in the examples section below, the conversion of PAA prodrugs to urinary PAGN was evaluated in subjects with HE. The mean percent conversion of PAA prodrug to urinary PAGN was found to be 57%, with a 95% confident interval range of 52-63%. This is significantly lower than the conversion percentage reported previously for HE patients in US Patent Publication No. 2010/0008859. US Patent Publication No. 2010/0008859 reports an overall mean conversion percentage of 60-75% in subjects with nitrogen retention disorders generally, and a mean conversion percentage of approximately 75% in HE patients specifically. In certain embodiments, this mean conversion percentage of PAA prodrug to urinary PAGN may be used alone or in combination with fasting blood ammonia level measurements and/or dietary protein intake measurements to treat HE using a PAA prodrug, administer a PAA prodrug, determine an effective dosage of a PAA prodrug, or evaluate or adjust the dosage of a PAA prodrug. In these embodiments, the mean percent conversion may be 50-65% or a percentage falling within this range (e.g., about 52 to 63%, 55 to 60%, 56 to 58%, 57%, etc.). In certain embodiments of the methods disclosed herein that take into account the mean percent conversion of PAA prodrug to urinary PAGN, the effective dosage is calculated based on a target nitrogen output. In certain embodiments, urinary PAGN may be determined as a ratio of the concentration of urinary PAGN to urinary creatinine.

In certain embodiments, methods are provided for calculating an effective initial dosage of a PAA prodrug for a subject with HE by determining a target urinary PAGN output and calculating the effective initial dosage based on the mean percent conversion of PAA prodrug to urinary PAGN as disclosed herein. In certain related embodiments, methods are provided for administering a PAA prodrug to a subject with HE or treating a subject having HE comprising (a) determining a target urinary PAGN output, (b) calculating an effective initial dosage of PAA prodrug based on the mean percent conversion of PAA prodrug to urinary PAGN, and (c) administering the effective initial dosage. In other embodiments, methods are provided for determining an effective dosage of a PAA prodrug for a subject with HE comprising (a) administering a first dosage, (b) measuring urinary PAGN output, and (c) determining an effective dosage based on the mean percent conversion of PAA prodrug to urinary PAGN as disclosed herein. In certain related embodiments, methods are provided for administering a PAA prodrug to a subject with HE comprising (a) administering a first dosage of PAA prodrug, (b) determining urinary PAGN output, (c) determining an effective dosage of the PAA prodrug based on the mean percent conversion of PAA prodrug to urinary PAGN, and (d) administering the effective dosage. In still other embodiments, methods are provided for determining whether to adjust a dosage of PAA prodrug based on the mean percent conversion of PAA prodrug to urinary PAGN as disclosed herein.

In certain embodiments, the percent conversion of PAA prodrug to urinary PAGN as disclosed herein may be incorporated into the methods set forth herein for treating HE, optimally administering a nitrogen scavenging drug for the treatment of HE, adjusting the dosage of a nitrogen scavenging drug for the treatment of HE, evaluating the efficacy of a nitrogen scavenging drug for the treatment of HE, determining whether to administer a nitrogen scavenging drug for the treatment of HE, or predicting the likelihood or risk of an HE event based on fasting blood ammonia level. In certain of these embodiments, the percent conversion of PAA prodrug to urinary PAGN as disclosed herein may be used to determine an effective initial dosage of PAA prodrug for treating HE, while the fasting ammonia level may be used to determine the efficacy of the initial dosage or to determine whether to adjust the dosage or administer a second PAA prodrug. In other embodiments, the percent conversion of PAA prodrug to urinary PAGN as disclosed herein and fasting ammonia level may both be taken into account when determining the optimal first or subsequent dosage of a PAA prodrug, adjusting the dosage of a PAA prodrug, evaluating the efficacy of a PAA prodrug, or determining whether to administer a PAA prodrug for the treatment of HE. In certain of these embodiments, the methods include steps of measuring fasting ammonia level and measuring urinary PAGN.

One skilled in the art will recognize that a variety of other factors may be taken into consideration when determining the effective dosage of a nitrogen scavenging drug. For example, factors such as diet (e.g., protein intake) and endogenous waste nitrogen removal capacity (e.g., urea synthesis capacity) may be considered.

Provided herein in certain embodiments are kits for carrying out the methods disclosed herein. In certain embodiments, kits are provided for evaluating the likelihood of a subject experiencing an HE event and for determining whether to administer a nitrogen scavenging drug or adjust the dosage of a nitrogen scavenging drug for a subject. The kits disclosed herein may include one or more nitrogen scavenging drugs and/or one or more reagents (e.g., bromophenol blue) or enzymes (e.g., glutamate dehydrogenase) to measure blood ammonia levels in a sample. The kit may additionally include other pigments, binders, surfactants, buffers, stabilizers, and/or chemicals necessary to obtain a blood sample and to measure the ammonia level in the sample. In certain embodiments, the kits provided herein comprise instructions in a tangible medium.

One of ordinary skill in the art will recognize that the various embodiments described herein can be combined. For example, steps from the various methods of treatment disclosed herein may be combined in order to achieve a satisfactory or improved level of treatment.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Predicting Future HE Events Based on Fasting Ammonia Levels

The relationship between HE events and fasting ammonia levels was evaluated in subjects from the HALT-HE clinical trial (HPN-100-008, ClinicalTrials.gov identifier NCT00999167). To be eligible for HE analysis, subject had to (1) be included in the HALT-HE (Part B) safety population, (2) have at least one treatment with a study drug (either HPN-100 or placebo), and (3) have a quantifiable measurement of plasma ammonia from a blood specimen drawn at the visit and time point of interest. Of the 178 total subjects enrolled in the HALT-HE study and included in the safety population, 171 met the additional criteria.

Fasting ammonia levels were measured on day 1 (baseline) and at days 7 and 14. Day 1 values were derived from the measurement closest to, but prior to, initiation of dosing. Day 7 and 14 values were obtained from the nominal visit day and time point (pre-dose or 4-hour). To account for differences in local laboratories used during the clinical trial, local measurements of ammonia were standardized to an upper limit of normal (ULN) of 35 μmol/L according to the following formula:

$$\text{Ammonia}_{std} = \text{Ammonia}_{local} * (35/\text{ULN of Ammonia}_{local}).$$

HE events were evaluated over 16 weeks. An HE event was defined as the occurrence of either (1) a West Haven Grade 2 or above or (2) a West Haven Grade 1 AND an asterixis grade increase of 1, if baseline West Haven was 0.

To describe the relationship between plasma ammonia levels and HE events, ammonia levels at the nominal times were initially grouped into five categories as multiples of the standardized ULN (35 μmol/L): (1) [0-≤0.5], (2) [0.5-≤1.0], (3) [1.0-≤1.5], (4) [1.5-≤2.0], and (5) [>2.0].

Each subject had between zero and eight HE episodes over the course of their exposure to study drug. The relationship between ammonia at a given nominal time and the number of HE events was modeled using a negative binomial model whereby the effect of study drug was considered only after controlling for ammonia level. Since not all subjects had the same amount of time in the study (and thus did not have the same opportunity for experiencing HE events), the model adjusted for (offset for) duration of treatment, measured in days and converted to weeks. Based on the model, the number of HE events was estimated for each level of ammonia. By comparing each level of ammonia to the lowest level, the pattern of the relationship could not only be described but also statistically tested through a priori contrasts.

For purposes of prediction, the number of HE events for each subject was categorized using two different outcome schemes: (1) a three category grouping (0 episodes, 1 episode, or 2 or more episodes) and (2) a two category grouping (0 episodes or 1 or more episodes). For the three category outcome scheme, the probability of having an outcome in one of the three categories based on ammonia level was modeled using ordered logistic regression following a proportional odds model (McCullagh and Nelder, Generalized Linear Models, 2nd ed. Boca Raton: Chapman and Hall, Ch. 5 (1989)). For the second scheme, probabilities of having an outcome in one of the two categories based on ammonia level were modeled using binary logistic regression. In each case, 95% confidence intervals of prediction around the probabilities were derived using bootstrap resampling of the original dataset with 1000 iterations following the technique of Davison and Hinkley (Bootstrap Methods and Their Application, Cambridge Univ. Press, pp. 358-362 (1997)).

Figure 2:
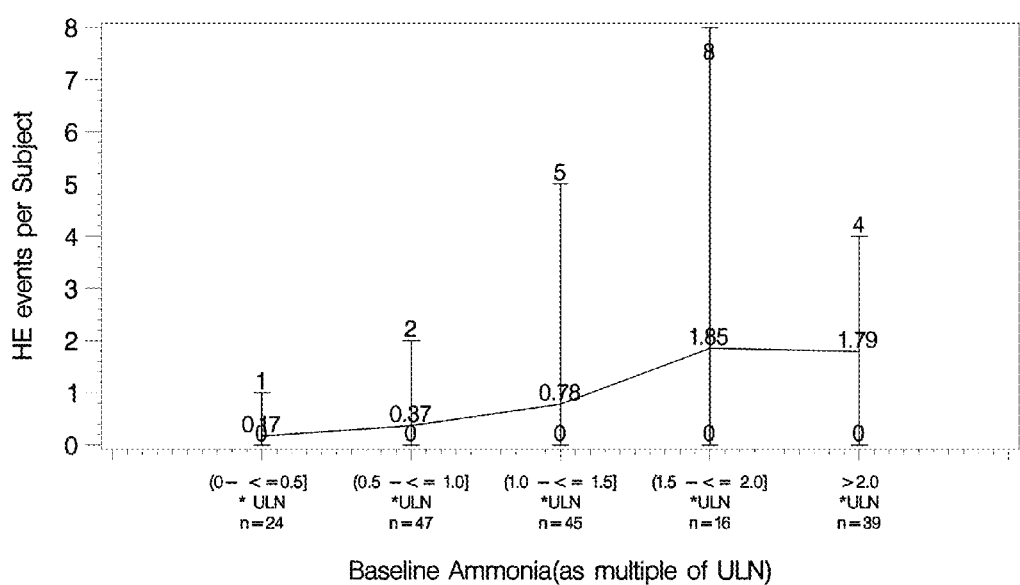
FIG. 2: Estimated number of HE events per subject over 16 weeks versus pre-dose plasma ammonia level on day 1 (baseline). Minimum and maximum observed plotted for reference. Levels 4 and 5 differ significantly from level 1 ($p=0.007$ and $p=0.002$, respectively).
Figure 3:
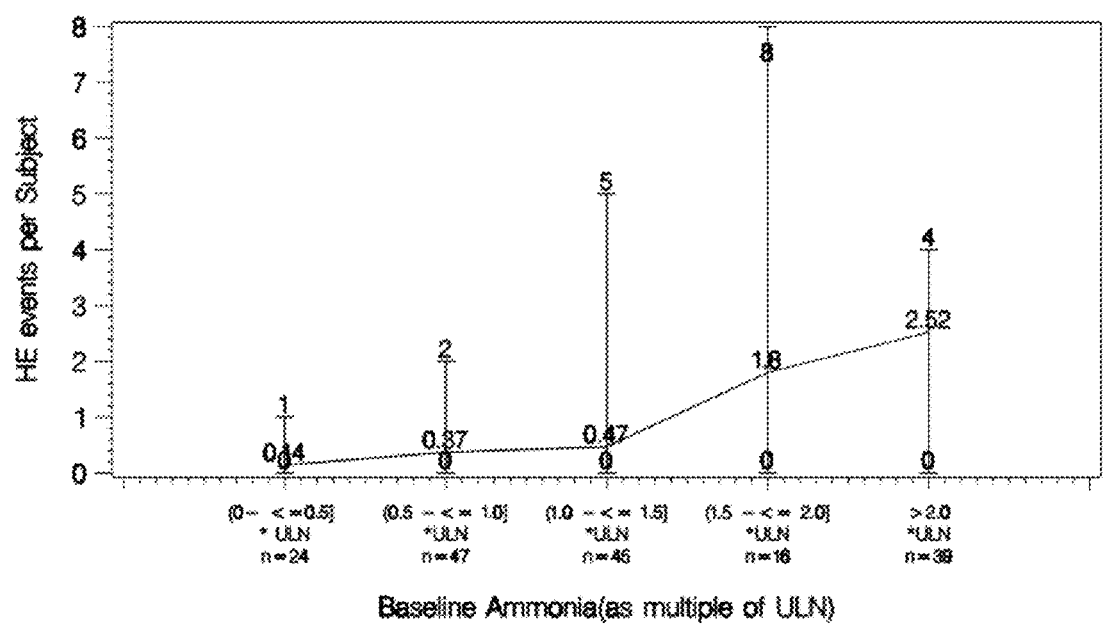
FIG. 3: Estimated number of HE events per subject over 16 weeks versus pre-dose plasma ammonia level on day 7. Minimum and maximum observed plotted for reference. Levels 4 and 5 differ significantly from level 1 ($p=0.0009$ and $p=0.0003$, respectively).
Figure 4:
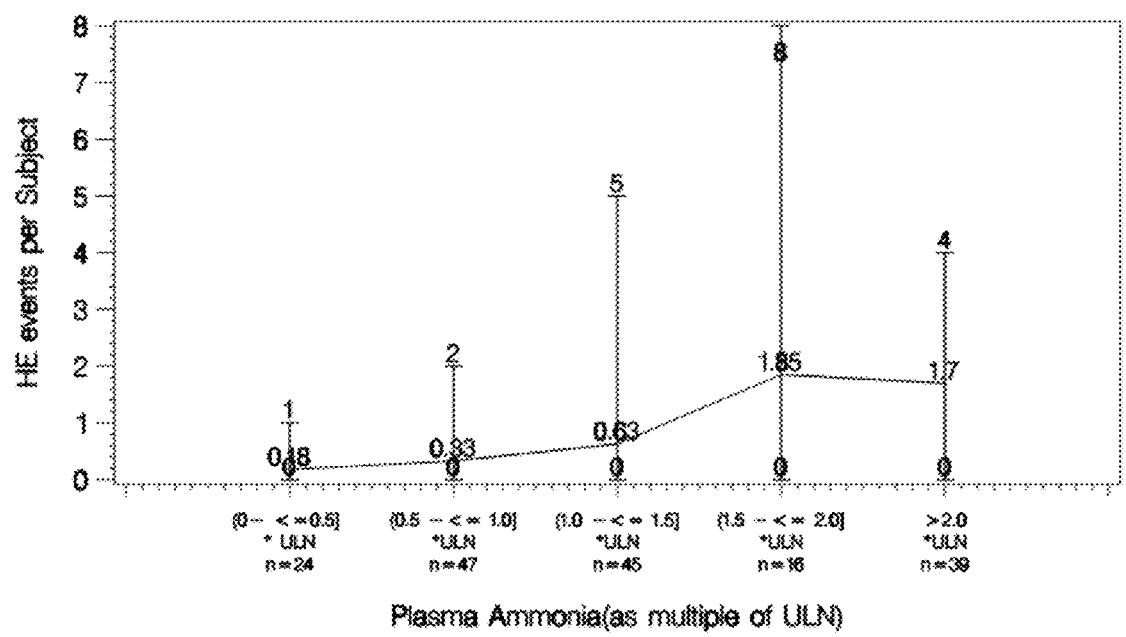
FIG. 4: Estimated number of HE events per subject over 16 weeks versus plasma ammonia level on day 7, four hours after dosing. Minimum and maximum observed plotted for reference. Levels 4 and 5 differ significantly from level 1 ($p=0.002$ and $p=0.001$, respectively).
Figure 5:
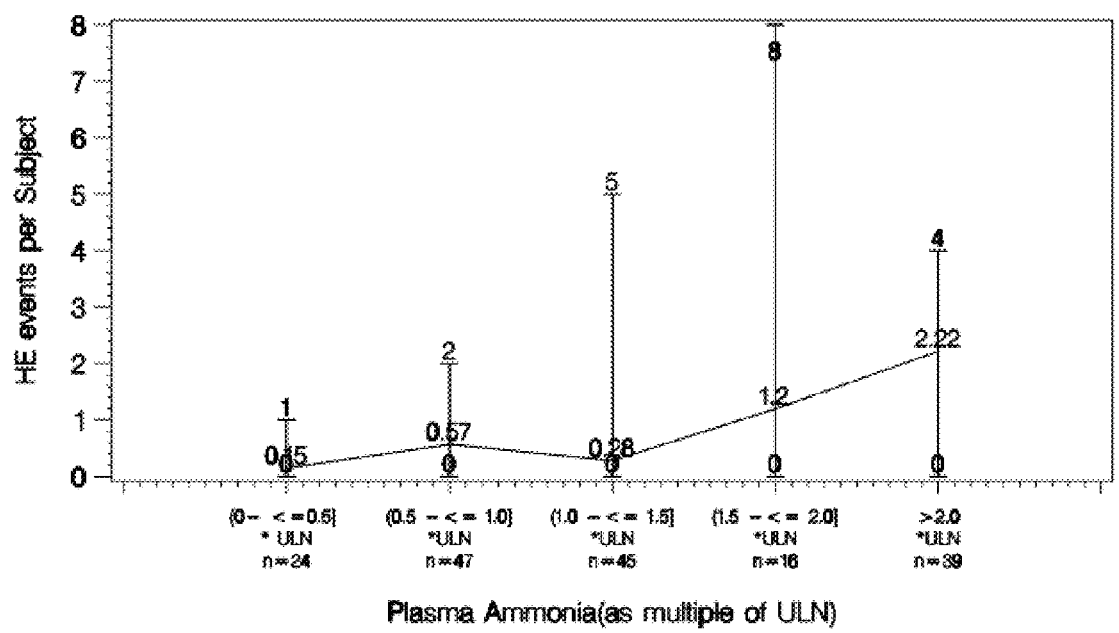
FIG. 5: Estimated number of HE events per subject over 16 weeks versus pre-dose plasma ammonia level on day 14. Minimum and maximum observed plotted for reference. Levels 4 and 5 differ significantly from level 1 ($p=0.014$ and $p=0.001$, respectively).
Figure 6:
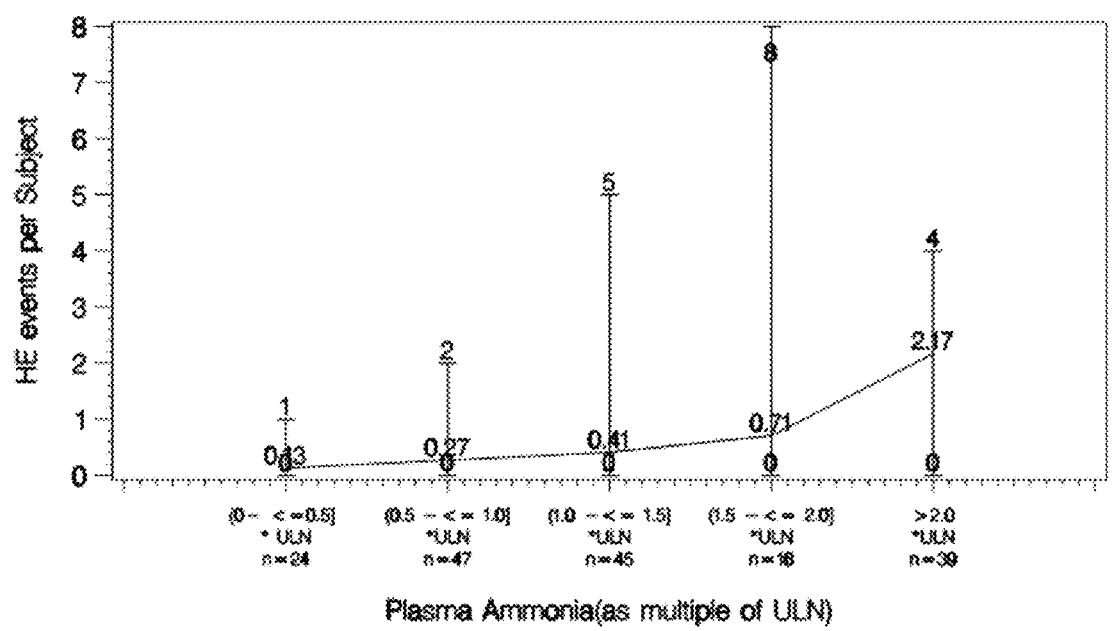
FIG. 6: Estimated number of HE events per subject over 16 weeks versus plasma ammonia level on day 14, four hours after dosing. Minimum and maximum observed plotted for reference. Level differs significantly from level 1 (p=0.002).

The relationship between HE events and ammonia levels at day 7 (pre-dose), day 7 (four hours after dosing), day 14 (pre-dose), and day 14 (four hours after dosing) for each of these groups is summarized in FIGS. 2-6. This analysis revealed no significant difference between the lowest two categories and between the highest two categories, so the categories were collapsed into two different grouping schemes for modeling purposes: (1) a three category grouping ([0-1.0], [>1.0-1.5], and [>1.5]) and 2) a two category grouping ([0-1.5] and [>1.5]). The relationship between HE events and ammonia levels at day 1, day 7 (pre-dose), day 7 (four hours after dosing), day 14 (pre-dose), and day 14 (four hours after dosing) for each of these groups is summarized in Tables 1-5, respectively. In each table, the first three rows for each treatment group show results for the three category model ([0-1.0], [>1.0-1.5], and [>1.5]), while the next two rows show results for the two category model ([0-1.5] and [>1.5]). Note that, based on the statistical methodology, estimation of HE events for input category >1.5 in a two category model is not necessarily equal to the result for the three category model.

TABLE 1

Count of HE events over 16 weeks by level of pre-dose ammonia on day 1:

| Treatment Group | Plasma ammonia level (as multiple of ULN) | N | Min | Max | Estimated* over 16 weeks | Estimated* over 52 weeks | p-value vs. lowest level | p-value main effect of drug | drug × ammonia interaction |
|---|---|---|---|---|---|---|---|---|---|
| HPN-100 | [0-1.0] | 37 | 0 | 2 | 0.25 | 0.80 | . | . | . |
|  | [>1.0-1.5] | 23 | 0 | 5 | 0.61 | 1.98 | 0.287 | . | . |
|  | [>1.5] | 26 | 0 | 4 | 1.35 | 4.37 | 0.031 | . | . |
|  | [0-1.5] | 60 | 0 | 5 | 0.39 | 1.26 | . | . | . |
|  | [>1.5] | 26 | 0 | 4 | 1.36 | 4.41 | 0.071 | . | . |
| Placebo | [0-1.0] | 34 | 0 | 2 | 0.37 | 1.21 | . | . | . |
|  | [>1.0-1.5] | 22 | 0 | 5 | 0.95 | 3.08 | 0.119 | . | . |
|  | [>1.5] | 29 | 0 | 8 | 2.20 | 7.14 | <.001 | . | . |

TABLE 1-continued

Count of HE events over 16 weeks by level of pre-dose ammonia on day 1:

| Treatment Group | Plasma ammonia level (as multiple of ULN) | N | Min | Max | Estimated* over 16 weeks | Estimated* over 52 weeks | p-value vs. lowest level | p-value main effect of drug | p-value drug × ammonia interaction |
|---|---|---|---|---|---|---|---|---|---|
|  | [0-1.5] | 56 | 0 | 5 | 0.59 | 1.90 | . | . | . |
|  | [>1.5] | 29 | 0 | 8 | 2.21 | 7.19 | 0.003 | . | . |
| TOTAL | [0-1.0] | 71 | 0 | 2 | 0.30 | 0.99 | . | 0.132 | 0.995 |
|  | [>1.0-1.5] | 45 | 0 | 5 | 0.78 | 2.55 | 0.054 | . | . |
|  | [>1.5] | 55 | 0 | 8 | 1.81 | 5.89 | <.001 | . | . |
|  | [0-1.5] | 116 | 0 | 5 | 0.48 | 1.57 | . | . | . |
|  | [>1.5] | 55 | 0 | 8 | 1.83 | 5.94 | <.001 | . | . |

TABLE 2

Count of HE events over 16 weeks by level of pre-dose ammonia on day 7:

| Treatment Group | Plasma Ammonia (as multiple of ULN) | N | Min | Max | Estimated* over 16 weeks | Estimated* over 52 weeks | p-value vs. lowest level | p-value main effect of drug | p-value drug × ammonia interaction |
|---|---|---|---|---|---|---|---|---|---|
| HPN-100 | [0-1.0] | 43 | 0 | 2 | 0.29 | 0.95 | . | . | . |
|  | [>1.0-1.5] | 17 | 0 | 5 | 0.90 | 2.92 | 0.174 | . | . |
|  | [>1.5] | 18 | 0 | 4 | 1.38 | 4.50 | 0.046 | . | . |
|  | [0-1.5] | 60 | 0 | 5 | 0.45 | 1.47 | . | . | . |
|  | [>1.5] | 18 | 0 | 4 | 1.40 | 4.56 | 0.134 | . | . |
| Placebo | [0-1.0] | 33 | 0 | 1 | 0.30 | 0.97 | . | . | . |
|  | [>1.0-1.5] | 19 | 0 | 2 | 0.23 | 0.73 | 0.699 | . | . |
|  | [>1.5] | 26 | 0 | 8 | 2.53 | 8.23 | <.001 | . | . |
|  | [0-1.5] | 52 | 0 | 2 | 0.27 | 0.88 | . | . | . |
|  | [>1.5] | 26 | 0 | 8 | 2.53 | 8.22 | <.001 | . | . |
| TOTAL | [0-1.0] | 76 | 0 | 2 | 0.29 | 0.94 | . | 0.920 | 0.124 |
|  | [>1.0-1.5] | 36 | 0 | 5 | 0.47 | 1.53 | 0.348 | . | . |
|  | [>1.5] | 44 | 0 | 8 | 2.10 | 6.84 | <.001 | . | . |
|  | [0-1.5] | 112 | 0 | 5 | 0.35 | 1.13 | . | . | . |
|  | [>1.5] | 44 | 0 | 8 | 2.11 | 6.85 | <.001 | . | . |

TABLE 3

Count of HE events over 16 weeks by level of ammonia on day 7, four hours post-dose:

| Treatment Group | Plasma Ammonia (as multiple of ULN) | N | Min | Max | Estimated* over 16 weeks | Estimated* over 52 weeks | p-value vs. lowest level | p-value main effect of drug | p-value drug × ammonia interaction |
|---|---|---|---|---|---|---|---|---|---|
| HPN-100 | [0-1.0] | 33 | 0 | 2 | 0.16 | 0.51 | . | . | . |
|  | [>1.0-1.5] | 20 | 0 | 5 | 0.88 | 2.85 | 0.048 | . | . |
|  | [>1.5] | 23 | 0 | 4 | 1.16 | 3.77 | 0.016 | . | . |
|  | [0-1.5] | 53 | 0 | 5 | 0.41 | 1.34 | . | . | . |
|  | [>1.5] | 23 | 0 | 4 | 1.18 | 3.85 | 0.145 | . | . |
| Placebo | [0-1.0] | 36 | 0 | 4 | 0.36 | 1.17 | . | . | . |
|  | [>1.0-1.5] | 12 | 0 | 2 | 0.36 | 1.16 | 0.999 | . | . |
|  | [>1.5] | 30 | 0 | 8 | 2.19 | 7.13 | <.001 | . | . |
|  | [0-1.5] | 48 | 0 | 4 | 0.36 | 1.16 | . | . | . |
|  | [>1.5] | 30 | 0 | 8 | 2.19 | 7.13 | <.001 | . | . |
| TOTAL | [0-1.0] | 69 | 0 | 4 | 0.27 | 0.87 | . | 0.275 | 0.249 |
|  | [>1.0-1.5] | 32 | 0 | 5 | 0.63 | 2.05 | 0.111 | . | . |
|  | [>1.5] | 53 | 0 | 8 | 1.76 | 5.72 | <.001 | . | . |
|  | [0-1.5] | 101 | 0 | 5 | 0.38 | 1.23 | . | . | . |
|  | [>1.5] | 53 | 0 | 8 | 1.77 | 5.74 | <.001 | . | . |

TABLE 4

Count of HE events over 16 weeks by level of ammonia on day 14:

| Treatment Group | Plasma Ammonia (as multiple of ULN) | N | Min | Max | Estimated* over 16 weeks | Estimated* over 52 weeks | p-value vs. lowest level | p-value main effect of drug | p-value drug × ammonia interaction |
|---|---|---|---|---|---|---|---|---|---|
| HPN-100 | [0-1.0] | 45 | 0 | 5 | 0.36 | 1.18 | . | . | . |
| | [>1.0-1.5] | 14 | 0 | 2 | 0.40 | 1.29 | 0.923 | . | . |
| | [>1.5] | 19 | 0 | 4 | 1.29 | 4.21 | 0.106 | . | . |
| | [0-1.5] | 59 | 0 | 5 | 0.37 | 1.21 | . | . | . |
| | [>1.5] | 19 | 0 | 4 | 1.29 | 4.21 | 0.096 | . | . |
| Placebo | [0-1.0] | 31 | 0 | 4 | 0.53 | 1.73 | . | . | . |
| | [>1.0-1.5] | 16 | 0 | 2 | 0.20 | 0.65 | 0.230 | . | . |
| | [>1.5] | 27 | 0 | 8 | 2.08 | 6.76 | 0.013 | . | . |
| | [0-1.5] | 47 | 0 | 4 | 0.41 | 1.32 | . | . | . |
| | [>1.5] | 27 | 0 | 8 | 2.08 | 6.77 | 0.001 | . | . |
| TOTAL | [0-1.0] | 76 | 0 | 5 | 0.43 | 1.41 | . | 0.428 | 0.579 |
| | [>1.0-1.5] | 30 | 0 | 2 | 0.28 | 0.92 | 0.474 | . | . |
| | [>1.5] | 46 | 0 | 8 | 1.77 | 5.74 | 0.002 | . | . |
| | [0-1.5] | 106 | 0 | 5 | 0.39 | 1.26 | . | . | . |
| | [>1.5] | 46 | 0 | 8 | 1.77 | 5.74 | <.001 | . | . |

TABLE 5

Count of HE events over 16 weeks by level of ammonia on day 14, four hours post-dose:

| Treatment Group | Plasma Ammonia (as multiple of ULN) | N | Min | Max | Estimated* over 16 weeks | Estimated* over 52 weeks | p-value vs. lowest level | p-value main effect of drug | p-value drug × ammonia interaction |
|---|---|---|---|---|---|---|---|---|---|
| HPN-100 | [0-1.0] | 35 | 0 | 4 | 0.28 | 0.92 | . | . | . |
| | [>1.0-1.5] | 22 | 0 | 2 | 0.41 | 1.33 | 0.688 | . | . |
| | [>1.5] | 17 | 0 | 4 | 0.96 | 3.13 | 0.210 | . | . |
| | [0-1.5] | 57 | 0 | 4 | 0.33 | 1.09 | . | . | . |
| | [>1.5] | 17 | 0 | 4 | 0.97 | 3.14 | 0.236 | . | . |
| Placebo | [0-1.0] | 35 | 0 | 1 | 0.20 | 0.65 | . | . | . |
| | [>1.0-1.5] | 7 | 0 | 1 | 0.47 | 1.52 | 0.360 | . | . |
| | [>1.5] | 34 | 0 | 8 | 1.97 | 6.40 | <.001 | . | . |
| | [0-1.5] | 42 | 0 | 1 | 0.25 | 0.81 | . | . | . |
| | [>1.5] | 34 | 0 | 8 | 1.97 | 6.42 | <.001 | . | . |
| TOTAL | [0-1.0] | 70 | 0 | 4 | 0.24 | 0.77 | . | 0.474 | 0.493 |
| | [>1.0-1.5] | 29 | 0 | 2 | 0.41 | 1.35 | 0.346 | . | . |
| | [>1.5] | 51 | 0 | 8 | 1.66 | 5.39 | <.001 | . | . |
| | [0-1.5] | 99 | 0 | 4 | 0.29 | 0.95 | . | . | . |
| | [>1.5] | 51 | 0 | 8 | 1.66 | 5.41 | <.001 | . | . |

As shown in these results, fasting ammonia levels were correlated with subsequent HE events over the 16 week exposure period. For example, subjects with a pre-dose ammonia level on day 1 that was less than or equal to the ULN (i.e., 0-1.0) experienced an estimated 0.30 events over 16 weeks. The number of events increased to 0.78 for subjects with pre-dose ammonia level of >1.0 to 1.5 ULN, and to 1.81 for subjects with ammonia levels greater than 1.5 ULN. The same pattern was observed in each study drug treatment arm.

The number of events in the highest level ammonia group (>1.5 ULN) was significantly greater than the number of events in the lowest level group (0 to 1.0 ULN) (p<0.001), and the number of events in the middle level ammonia group (>1.0 to 1.5 ULN) was marginally greater than the number of events in the lowest level group (p=0.054). These results show that the risk of an HE event does not increase linearly with increasing ammonia level. Instead, there appears to be a step up in the risk for baseline ammonia levels greater than 1.5 times the ULN. This trend appears to be evident regardless of which visit and time the ammonia was drawn.

The proportional odds of experiencing an HE for various ammonia levels at day 1, day 7 (pre-dose), day 7 (four hours after dosing), day 14 (pre-dose), and day 14 (four hours after dosing) are summarized in Tables 6-10, respectively. Levels 1, 2, and 4 in each table show the results for the three category model ([0-1.0], [>1.0-1.5], and [>1.5]), while levels 3 and 4 show the results for the two category model ([0-1.5] and [>1.5]).

TABLE 6

Probably of HE events over 16 weeks as predicted by level of pre-dose ammonia on day 1:

| Plasma ammonia as predictor | | | | | | p-value |
|---|---|---|---|---|---|---|
| | Plasma Ammonia | Prob. of having this number of HE events (95% CI) | | | | vs. next |
| Level | (as multiple of ULN) | 0 events | 1 event | 2 or more events | 1 or more events | lower level |
| 1 | [0-1.0] | 0.812 (0.722, 0.896) | 0.114 (0.059, 0.180) | 0.074 (0.037, 0.113) | 0.197 (0.107, 0.297) | |
| 2 | [>1.0-1.5] | 0.758 (0.627, 0.883) | 0.143 (0.070, 0.220) | 0.099 (0.040, 0.174) | 0.244 (0.116, 0.376) | 0.547 |
| 3 | [0-1.5] | 0.792 (0.721, 0.865) | 0.125 (0.071, 0.181) | 0.083 (0.049, 0.120) | 0.216 (0.138, 0.289) | |
| 4 | [>1.5] | 0.529 (0.386, 0.672) | 0.236 (0.161, 0.319) | 0.235 (0.124, 0.359) | 0.436 (0.306, 0.574) | 0.003 |

TABLE 7

Probably of HE events over 16 weeks as predicted by level of pre-dose ammonia on day 7:

| Plasma ammonia as predictor | | | | | | p-value |
|---|---|---|---|---|---|---|
| | Plasma Ammonia | Prob. of having this number of HE events (95% CI) | | | | vs. next |
| Level | (as multiple of ULN) | 0 events | 1 event | 2 or more events | 1 or more events | lower level |
| 1 | [0-1.0] | 0.812 (0.732, 0.889) | 0.118 (0.064, 0.182) | 0.070 (0.038, 0.106) | 0.197 (0.114, 0.285) | |
| 2 | [>1.0-1.5] | 0.830 (0.692, 0.944) | 0.108 (0.040, 0.184) | 0.063 (0.017, 0.132) | 0.167 (0.055, 0.293) | 0.698 |
| 3 | [0-1.5] | 0.817 (0.750, 0.882) | 0.115 (0.069, 0.168) | 0.068 (0.039, 0.104) | 0.188 (0.120, 0.257) | |
| 4 | [>1.5] | 0.466 (0.318, 0.617) | 0.262 (0.176, 0.351) | 0.272 (0.148, 0.406) | 0.500 (0.356, 0.646) | <0.001 |

TABLE 8

Probably of HE events over 16 weeks as predicted by level of ammonia on day 7, four hours post-dose:

| Plasma ammonia as predictor | | | | | | p-value |
|---|---|---|---|---|---|---|
| | Plasma Ammonia | Prob. of having this number of HE events (95% CI) | | | | vs. next |
| Level | (as multiple of ULN) | 0 events | 1 event | 2 or more events | 1 or more events | lower level |
| 1 | [0-1.0] | 0.846 (0.769, 0.921) | 0.091 (0.044, 0.151) | 0.063 (0.031, 0.098) | 0.159 (0.081, 0.246) | |
| 2 | [>1.0-1.5] | 0.754 (0.611, 0.900) | 0.138 (0.059, 0.218) | 0.108 (0.038, 0.198) | 0.250 (0.100, 0.403) | 0.282 |
| 3 | [0-1.5] | 0.817 (0.746, 0.886) | 0.106 (0.060, 0.162) | 0.077 (0.043, 0.115) | 0.188 (0.117, 0.263) | |
| 4 | [>1.5] | 0.540 (0.402, 0.675) | 0.220 (0.147, 0.301) | 0.240 (0.131, 0.357) | 0.434 (0.305, 0.566) | 0.001 |

TABLE 9

Probably of HE events over 16 weeks as predicted by level of pre-dose ammonia on day 14:

| Plasma ammonia as predictor | | | | | | p-value |
|---|---|---|---|---|---|---|
| | Plasma Ammonia | Prob. of having this number of HE events (95% CI) | | | | vs. next |
| Level | (as multiple of ULN) | 0 events | 1 event | 2 or more events | 1 or more events | lower level |
| 1 | [0-1.0] | 0.812 (0.731, 0.888) | 0.104 (0.055, 0.163) | 0.084 (0.047, 0.126) | 0.197 (0.116, 0.287) | |
| 2 | [>1.0-1.5] | 0.834 (0.699, 0.945) | 0.093 (0.026, 0.169) | 0.073 (0.018, 0.144) | 0.167 (0.054, 0.309) | 0.716 |

TABLE 9-continued

Probably of HE events over 16 weeks as predicted by level of pre-dose ammonia on day 14:

| Plasma ammonia as predictor | | | | | | p-value |
|---|---|---|---|---|---|---|
| | Plasma Ammonia | Prob. of having this number of HE events (95% CI) | | | | vs. next |
| Level | (as multiple of ULN) | 0 events | 1 event | 2 or more events | 1 or more events | lower level |
| 3 | [0-1.5] | 0.818 (0.747, 0.884) | 0.101 (0.055, 0.154) | 0.081 (0.049, 0.117) | 0.189 (0.118, 0.263) | |
| 4 | [>1.5] | 0.525 (0.377, 0.678) | 0.211 (0.136, 0.287) | 0.264 (0.134, 0.398) | 0.435 (0.298, 0.571) | 0.002 |

TABLE 10

Probably of HE events over 16 weeks as predicted by level of ammonia on day 14, four hours post-dose:

| Plasma ammonia as predictor | | | | | | p-value |
|---|---|---|---|---|---|---|
| | Plasma Ammonia | Prob. of having this number of HE events (95% CI) | | | | vs. next |
| Level | (as multiple of ULN) | 0 events | 1 event | 2 or more events | 1 or more events | lower level |
| 1 | [0-1.0] | 0.874 (0.801, 0.941) | 0.075 (0.032, 0.129) | 0.051 (0.022, 0.086) | 0.129 (0.061, 0.203) | |
| 2 | [>1.0-1.5] | 0.738 (0.596, 0.880) | 0.145 (0.068, 0.234) | 0.117 (0.043, 0.203) | 0.276 (0.121, 0.444) | 0.083 |
| 3 | [0-1.5] | 0.834 (0.764, 0.896) | 0.097 (0.053, 0.154) | 0.070 (0.039, 0.108) | 0.172 (0.106, 0.245) | |
| 4 | [>1.5] | 0.561 (0.425, 0.699) | 0.213 (0.138, 0.293) | 0.226 (0.120, 0.346) | 0.412 (0.285, 0.535) | 0.002 |

Figure 7:
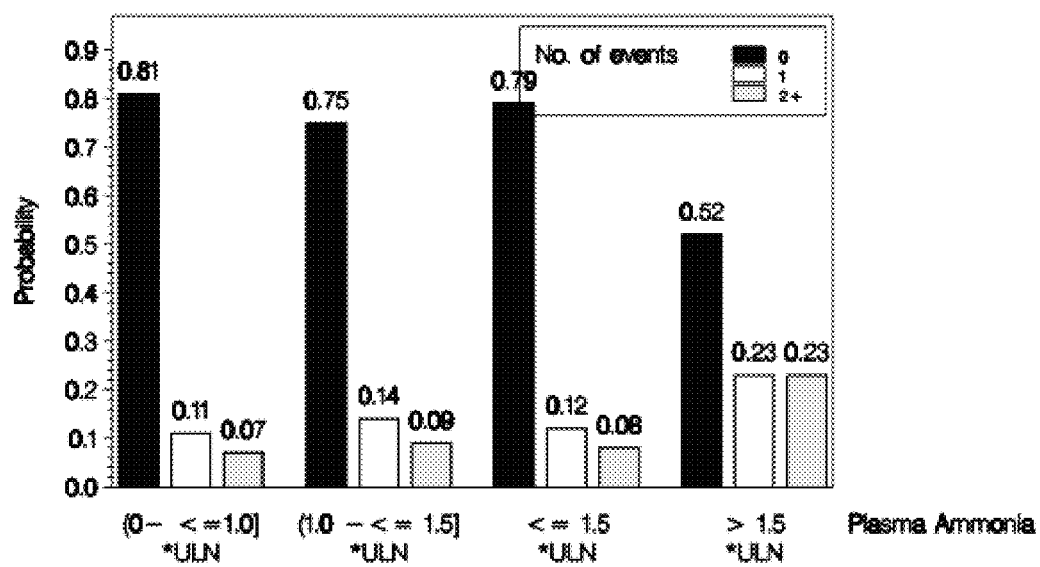
FIG. 7: Probability of having 0, 1, or 2 or more HE events over 16 weeks as predicted by plasma ammonia levels at baseline (day 1, pre-dose).
Figure 8:
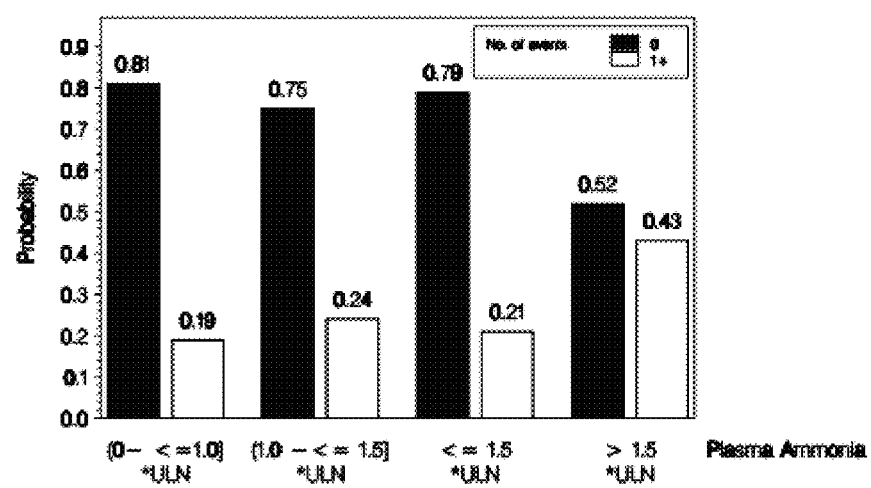
FIG. 8: Probability of having 0 or 1 or more HE events over 16 weeks as predicted by plasma ammonia levels at baseline (day 1, pre-dose).
Figure 9:
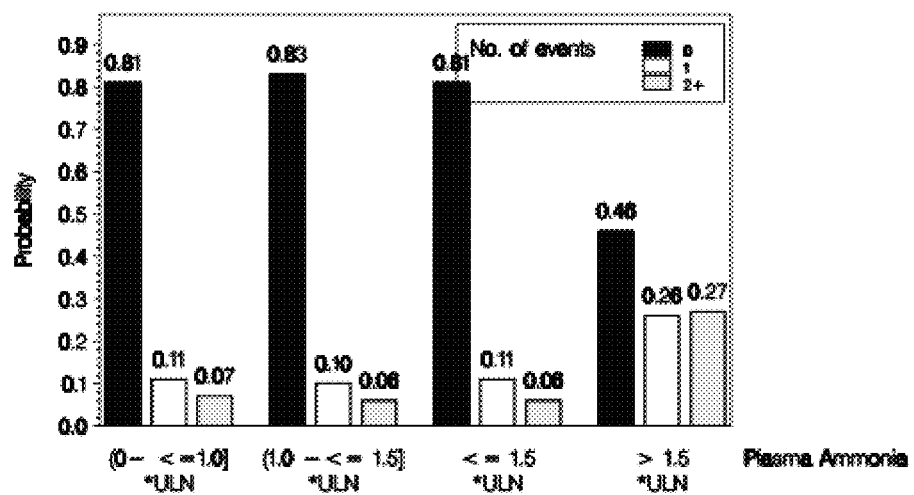
FIG. 9: Probability of having 0, 1, or 2 or more HE events over 16 weeks as predicted by plasma ammonia levels (day 7, pre-dose).
Figure 10:
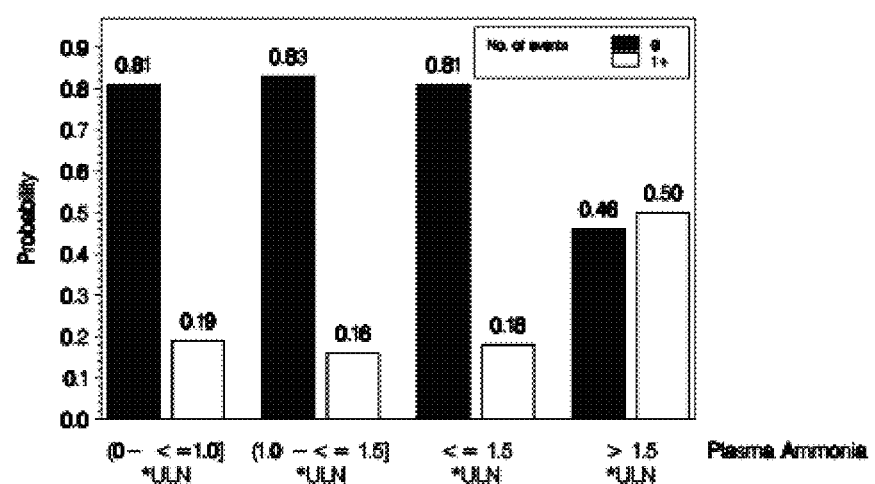
FIG. 10: Probability of having 0 or 1 or more HE events over 16 weeks as predicted by plasma ammonia levels (day 7, pre-dose).

Among subjects whose ammonia levels were normal pre-dose on day 1 (i.e., 0 to 1.0 ULN), 81% are expected to have no HE events within 16 weeks and 7% are expected to have two or more HE events (Table 6). Among subject with day 1 pre-dose ammonia levels greater than 1.5 ULN, on the other hand, only 52% are expected to have zero HE events within 16 weeks and 23% are expected to have two or more HE events. As illustrated in the baseline and day 7 results summarized in FIGS. 7-10, this pattern was consistent regardless of whether blood samples were drawn prior to the study or during the study.

Example 2

Conversion of PAA Prodrug to Urinary PAGN

US Patent Publication No. 2010/0008859 discloses that urinary PAGN levels correlate more closely to PBA prodrug dosage than plasma PAA, PBA, or PAGN levels, and further discloses that PBA prodrugs are converted to urinary PAGN with a mean efficiency of 60 to 75%. This conversion percentage is based on data obtained from subjects with UCD and HE. For HE subjects, PAA metabolism was evaluated by administering HPN-100 to 32 subjects with hepatic impairment with cirrhosis. The subjects were broken into four groups of 8 subjects each: hepatic impairment with cirrhosis and Child-Pugh scores of A, B, or C, and a control group of healthy adults with normal hepatic function. The mean percent conversion of HPN-100 to urinary PAGN in these four patient groups was of 79.6% (SD=30.5), 58.2% (SD=29.2), 85.0% (SD=65.1), and 68.6% (SD=21.9), respectively. The overall mean percent conversion for the four subject groups was about 75%.

PAA prodrug conversion has now been evaluated in additional HE subjects. These results unexpectedly show that the percent conversion of PAA prodrug to urinary PAGN is lower than disclosed in Patent Publication No. 2010/0008859.

As disclosed herein, additional trials have been performed to evaluate the conversion of PAA to urinary PAGN in subjects with HE. Urinary PAGN output was measured in 130 HE patients during steady state dosing with either NaPBA or an equivalent dose of HPN-100. As summarized in Table 11, the mean percent conversion of PAA prodrug to urinary PAGN in HE patients was about 57%, with a 95% confidence interval range of 52-63%. Results were consistent for both sodium PBA and HPN-100, indicating that similar results would be expected for all PAA prodrugs. These results suggest that the percent conversion of PAA prodrug to urinary PAGN in subjects with HE is significantly lower than previously reported in US Patent Publication No. 2010/0008859.

TABLE 11

| Mean percent conversion of PAA prodrugs to urinary PAGN in subjects with HE: | |
|---|---|
| N | 130 |
| Mean % conversion | 57% |
| 95% CI range | 52-62% |

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Brusilow Science 207:659 (1980)
2. Brusilow Pediatr Res 29:147 (1991)
3. Diaz Mol Genet Metab 102:276 (2011)
4. Ghabril Gastroenterology 142:S918 (2012)
5. Lee Mol Genet Metab 100:221 (2010)
6. Lichter-Konecki Mol Genet Metab 103:323 (2011)
7. McGuire Hepatology 51:2077 (2010)
8. Rockey Hepatology 56:248 (2012)

What is claimed is:

1. A method of treating hepatic encephalopathy (HE) in a subject comprising:
   (a) measuring a fasting blood ammonia level;
   (b) comparing the fasting blood ammonia level to the upper limit of normal for blood ammonia; and
   (c) administering glyceryl tri-[4-phenylbutyrate] (HPN-100) to the subject if the fasting blood ammonia level is greater than 1.5 times the upper limit of normal for blood ammonia.

2. The method of claim 1, wherein the subject has previously been administered a first dosage of glyceryl tri-[4-phenylbutyrate] (HPN-100).

3. The method of claim 2, wherein the dosage of glyceryl tri-[4-phenylbutyrate] (HPN-100) administered in step (c) is greater than the first dosage.

4. A method of optimizing the dosage of a nitrogen scavenging drug for the treatment of hepatic encephalopathy (HE) comprising:
   (a) administering a first dosage of glyceryl tri-[4-phenylbutyrate] (HPN-100);
   (b) measuring a fasting blood ammonia level;
   (c) comparing the fasting blood ammonia level to the upper limit of normal for blood ammonia to determine whether to increase the dosage of glyceryl tri-[4-phenylbutyrate] (HPN-100), wherein the dosage needs to be increased if the fasting blood ammonia level is greater than 1.5 times the upper limit of normal for blood ammonia; and
   (d) administering a second dosage of glyceryl tri-[4-phenylbutyrate] (HPN-100) based on the determination in (c).

5. The method of claim 1 or 4, further comprising a step of determining the upper limit of normal for blood ammonia for the subject.

6. The method of claim 1 or 4, wherein the upper limit of normal blood ammonia is 35 µmol/L.

* * * * *